(12) United States Patent
Jackson et al.

(10) Patent No.: US 9,883,892 B2
(45) Date of Patent: *Feb. 6, 2018

(54) POLYAXIAL BONE ANCHOR WITH POP-ON SHANK, FRICTION FIT RETAINER, WINGED INSERT AND LOW PROFILE EDGE LOCK

(71) Applicant: Roger P. Jackson, Prairie Village, KS (US)

(72) Inventors: Roger P. Jackson, Prairie Village, KS (US); James L. Surber, Kansas City, KS (US)

(73) Assignee: Roger P. Jackson, Prairie Village, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 15/338,817

(22) Filed: Oct. 31, 2016

(65) Prior Publication Data

US 2017/0042586 A1    Feb. 16, 2017

Related U.S. Application Data

(63) Continuation of application No. 13/573,874, filed on Oct. 10, 2012, now Pat. No. 9,480,517, which is a
(Continued)

(51) Int. Cl.
| | |
|---|---|
| A61B 17/70 | (2006.01) |
| A61B 17/86 | (2006.01) |
| A61B 90/00 | (2016.01) |
| A61B 17/56 | (2006.01) |
| A61B 17/68 | (2006.01) |

(52) U.S. Cl.
CPC ........ *A61B 17/7037* (2013.01); *A61B 17/702* (2013.01); *A61B 17/7005* (2013.01); *A61B 17/7008* (2013.01); *A61B 17/7038* (2013.01); *A61B 17/7082* (2013.01); *A61B 17/7091* (2013.01); *A61B 17/864* (2013.01); *A61B 2017/567* (2013.01); *A61B 2017/681* (2013.01);
(Continued)

(58) Field of Classification Search
CPC ............ A61B 17/7037; A61B 17/7005; A61B 17/7008; A61B 17/702; A61B 17/7038; A61B 17/7082; A61B 17/7091; A61B 17/864; A61B 2090/0808; A61B 2017/567; A61B 2017/681; Y10T 29/49826
USPC .......................... 606/246–279, 300–309, 328
See application file for complete search history.

(56) References Cited

U.S. PATENT DOCUMENTS

| | | |
|---|---|---|
| 5,501,684 A | 3/1996 | Schlapfer |
| 5,735,853 A | 4/1998 | Olerud |

(Continued)

*Primary Examiner* — Pedro Philogene
(74) *Attorney, Agent, or Firm* — Polsinelli PC

(57) ABSTRACT

A polyaxial bone screw assembly includes a threaded shank body having an integral upper portion receivable in an integral receiver, the receiver having an upper channel for receiving a longitudinal connecting member and a lower cavity cooperating with a lower opening. A down-loadable compression insert, a down-loadable friction fit split retaining ring having inner and outer tangs and an up-loadable shank upper portion cooperate to provide for pop- or snap-on assembly of the shank with the receiver either prior to or after implantation of the shank into a vertebra. The shank and receiver once assembled cannot be disassembled.

23 Claims, 17 Drawing Sheets

Related U.S. Application Data continuation-in-part of application No. 13/573,516, filed on Sep. 19, 2012, and a continuation-in-part of application No. 13/374,439, filed on Dec. 29, 2011, and a continuation-in-part of application No. 13/373,289, filed on Nov. 9, 2011, and a continuation-in-part of application No. 13/136,331, filed on Jul. 28, 2011, now abandoned, and a continuation-in-part of application No. 13/573,303, filed on Sep. 7, 2012, now Pat. No. 9,393,047, and a continuation-in-part of application No. 13/506,365, filed on Apr. 13, 2012, now Pat. No. 8,444,681, and a continuation-in-part of application No. 13/385,212, filed on Feb. 8, 2012, now Pat. No. 9,216,041, and a continuation-in-part of application No. 12/924,802, filed on Oct. 5, 2010, now Pat. No. 8,556,938, and a continuation-in-part of application No. 12/802,849, filed on Jun. 15, 2010.

(60) Provisional application No. 61/627,374, filed on Oct. 11, 2011, provisional application No. 61/626,250, filed on Sep. 23, 2011, provisional application No. 61/460,267, filed on Dec. 29, 2010, provisional application No. 61/463,037, filed on Feb. 11, 2011, provisional application No. 61/456,649, filed on Nov. 10, 2010, provisional application No. 61/460,234, filed on Dec. 29, 2010, provisional application No. 61/400,504, filed on Jul. 29, 2010, provisional application No. 61/403,915, filed on Sep. 23, 2010, provisional application No. 61/573,508, filed on Sep. 7, 2011, provisional application No. 61/517,088, filed on Apr. 13, 2011, provisional application No. 61/278,240, filed on Oct. 5, 2009, provisional application No. 61/336,911, filed on Jan. 28, 2010, provisional application No. 61/343,737, filed on May 3, 2010, provisional application No. 61/395,564, filed on May 14, 2010, provisional application No. 61/395,752, filed on May 17, 2010, provisional application No. 61/396,390, filed on May 26, 2010, provisional application No. 61/398,807, filed on Jul. 1, 2010, provisional application No. 61/402,959, filed on Sep. 8, 2010, provisional application No. 61/403,696, filed on Sep. 20, 2010, provisional application No. 61/268,708, filed on Jun. 15, 2009, provisional application No. 61/270,754, filed on Jul. 13, 2009.

(52) U.S. Cl.
CPC . *A61B 2090/0808* (2016.02); *Y10T 29/49826* (2015.01)

(56) References Cited

U.S. PATENT DOCUMENTS

| | | | |
|---|---|---|---|
| 5,891,145 A | 4/1999 | Morrison et al. | |
| 6,063,090 A | 5/2000 | Schlapfer | |
| 6,146,383 A | 11/2000 | Studer et al. | |
| 6,241,731 B1 | 6/2001 | Fiz | |
| 6,280,442 B1 | 8/2001 | Barker et al. | |
| 6,648,888 B1 | 11/2003 | Shluzas | |
| 6,660,004 B2 | 12/2003 | Barker et al. | |
| 6,716,214 B1 | 4/2004 | Jackson | |
| 6,740,086 B2 | 5/2004 | Richelsoph | |
| 7,001,389 B1 | 2/2006 | Navarro et al. | |
| 7,066,937 B2 | 6/2006 | Shluzas | |
| 7,186,255 B2 | 3/2007 | Baynham | |
| 7,306,606 B2 | 12/2007 | Sasing | |
| 7,322,981 B2 | 1/2008 | Jackson | |
| 7,530,992 B2 | 5/2009 | Biedermann et al. | |
| 7,625,396 B2 | 12/2009 | Jackson | |
| 7,776,067 B2 | 8/2010 | Jackson | |
| 7,833,251 B1 | 11/2010 | Ahlgren et al. | |
| 7,857,834 B2 | 12/2010 | Boschert | |
| 7,875,065 B2 | 1/2011 | Jackson | |
| 7,922,748 B2 | 4/2011 | Hoffman | |
| 7,947,065 B2 | 5/2011 | Hammill et al. | |
| 8,021,397 B2 | 9/2011 | Farris et al. | |
| 8,034,089 B2 | 10/2011 | Matthis et al. | |
| 8,048,126 B2 | 11/2011 | Altarac et al. | |
| 8,066,744 B2 | 11/2011 | Justis et al. | |
| 8,133,262 B2 * | 3/2012 | Whipple | A61B 17/7037 606/265 |
| 8,137,386 B2 | 3/2012 | Jackson | |
| 8,206,422 B2 | 6/2012 | Hestad et al. | |
| 9,393,047 B2 | 9/2012 | Jackson et al. | |
| 8,277,485 B2 | 10/2012 | Krishna et al. | |
| 8,361,129 B2 | 1/2013 | Chao | |
| 8,430,914 B2 | 4/2013 | Spratt et al. | |
| 8,506,609 B2 | 8/2013 | Biedermann et al. | |
| 8,591,558 B2 | 11/2013 | Matthis et al. | |
| 8,986,349 B1 * | 3/2015 | German | A61B 17/7068 606/279 |
| 9,168,069 B2 * | 10/2015 | Jackson | A61B 17/7037 |
| 2002/0026193 A1 | 2/2002 | Barker et al. | |
| 2002/0143341 A1 | 10/2002 | Biedermann et al. | |
| 2004/0267264 A1 | 12/2004 | Konieczynski et al. | |
| 2005/0080415 A1 | 4/2005 | Keyer et al. | |
| 2006/0155277 A1 | 7/2006 | Metz-Stavenhagen | |
| 2006/0200131 A1 * | 9/2006 | Chao | A61B 17/7037 606/278 |
| 2007/0088357 A1 | 4/2007 | Johnson et al. | |
| 2007/0090238 A1 | 4/2007 | Justis | |
| 2007/0093826 A1 | 4/2007 | Hawkes et al. | |
| 2007/0093827 A1 | 4/2007 | Warnick | |
| 2007/0118117 A1 | 5/2007 | Altarac et al. | |
| 2007/0118123 A1 | 5/2007 | Strausbaugh et al. | |
| 2007/0123862 A1 | 5/2007 | Warnick | |
| 2007/0233087 A1 | 10/2007 | Schlapfer | |
| 2007/0270813 A1 | 11/2007 | Garamszegi | |
| 2007/0270831 A1 | 11/2007 | Dewey et al. | |
| 2008/0132957 A1 | 6/2008 | Matthis et al. | |
| 2008/0140135 A1 | 6/2008 | Konieczynski et al. | |
| 2008/0140136 A1 | 6/2008 | Jackson | |
| 2008/0147129 A1 | 6/2008 | Biedermann et al. | |
| 2008/0161863 A1 | 7/2008 | Arnold et al. | |
| 2008/0215100 A1 | 9/2008 | Matthis et al. | |
| 2008/0234761 A1 | 9/2008 | Jackson | |
| 2008/0269809 A1 | 10/2008 | Garamszegi | |
| 2008/0319490 A1 | 12/2008 | Jackson | |
| 2009/0062867 A1 | 3/2009 | Schumacher | |
| 2009/0069852 A1 | 3/2009 | Farris et al. | |
| 2009/0105769 A1 | 4/2009 | Rock et al. | |
| 2009/0204155 A1 | 8/2009 | Aschmann | |
| 2010/0023061 A1 | 1/2010 | Randol et al. | |
| 2010/0094343 A1 | 4/2010 | Pham et al. | |
| 2010/0094349 A1 | 4/2010 | Hammer et al. | |
| 2010/0100137 A1 | 4/2010 | Justis et al. | |
| 2010/0152787 A1 | 6/2010 | Walsh et al. | |
| 2010/0234902 A1 | 9/2010 | Biedermann et al. | |
| 2010/0256686 A1 | 10/2010 | Fisher | |
| 2010/0262195 A1 | 10/2010 | Jackson | |
| 2010/0274288 A1 | 10/2010 | Prevost et al. | |
| 2010/0305621 A1 | 12/2010 | Wang et al. | |
| 2012/0010661 A1 | 1/2012 | Farris et al. | |
| 2012/0046700 A1 | 2/2012 | Jackson et al. | |
| 2012/0059426 A1 | 3/2012 | Jackson et al. | |
| 2012/0143266 A1 | 6/2012 | Jackson et al. | |
| 2013/0046350 A1 | 10/2012 | Jackson et al. | |
| 2013/0023941 A1 | 1/2013 | Jackson et al. | |
| 2013/0296951 A1 | 5/2013 | Jackson et al. | |
| 2014/0128927 A1 | 10/2013 | Jackson | |
| 2016/0051290 A1 | 10/2015 | Jackson et al. | |
| 2016/0354121 A1 | 12/2016 | Jackson | |

* cited by examiner

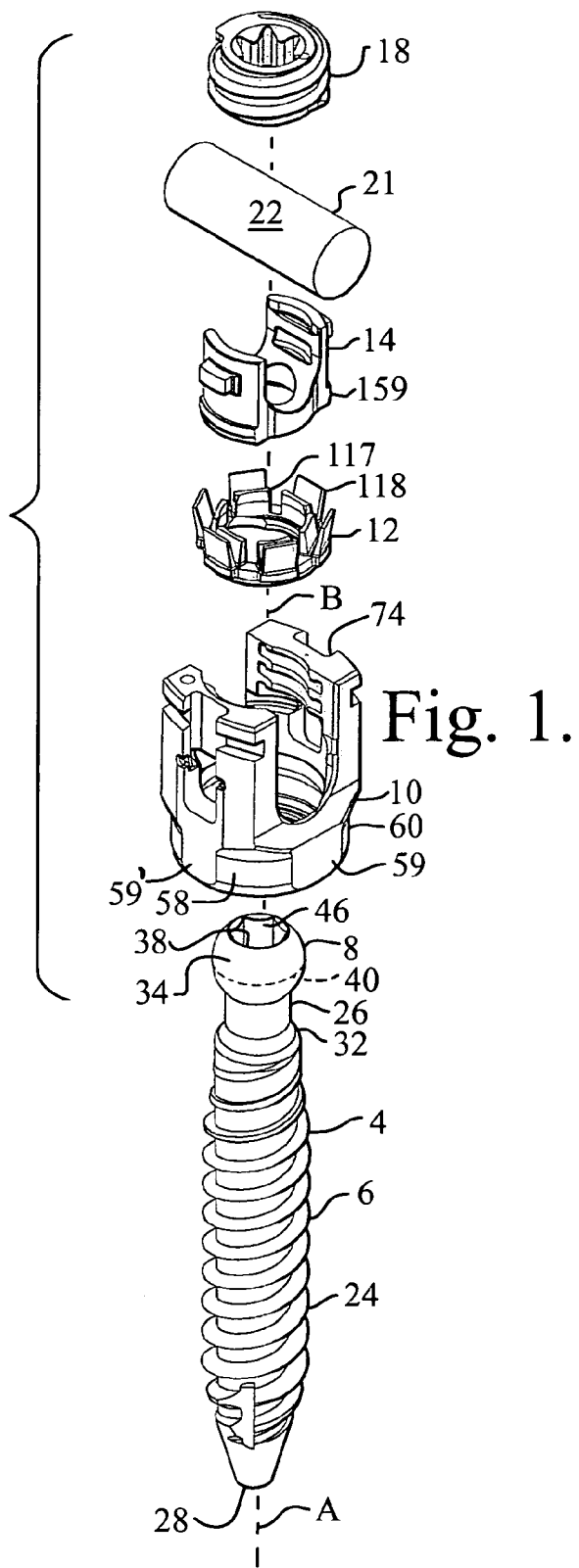
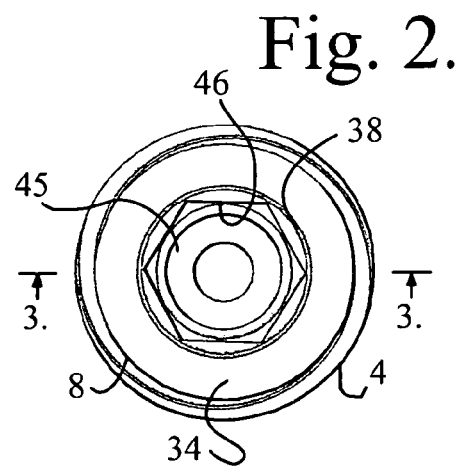
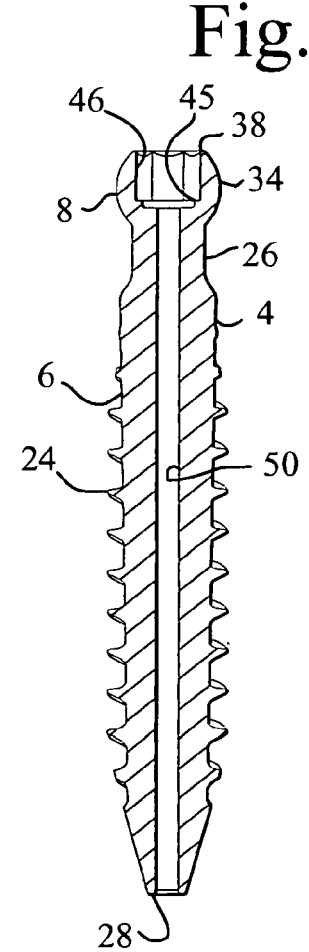
Fig. 1.
Fig. 2.
Fig. 3.

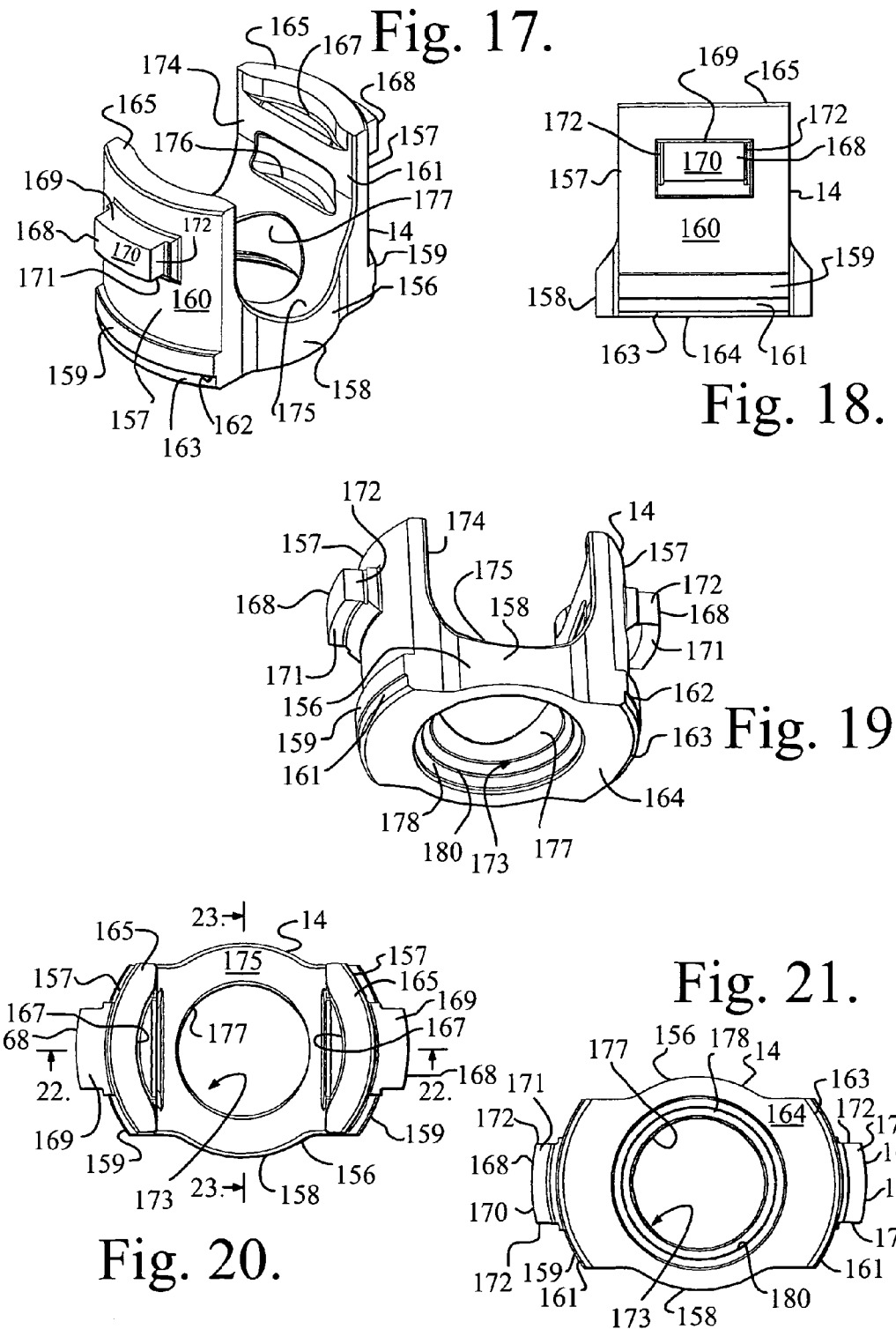

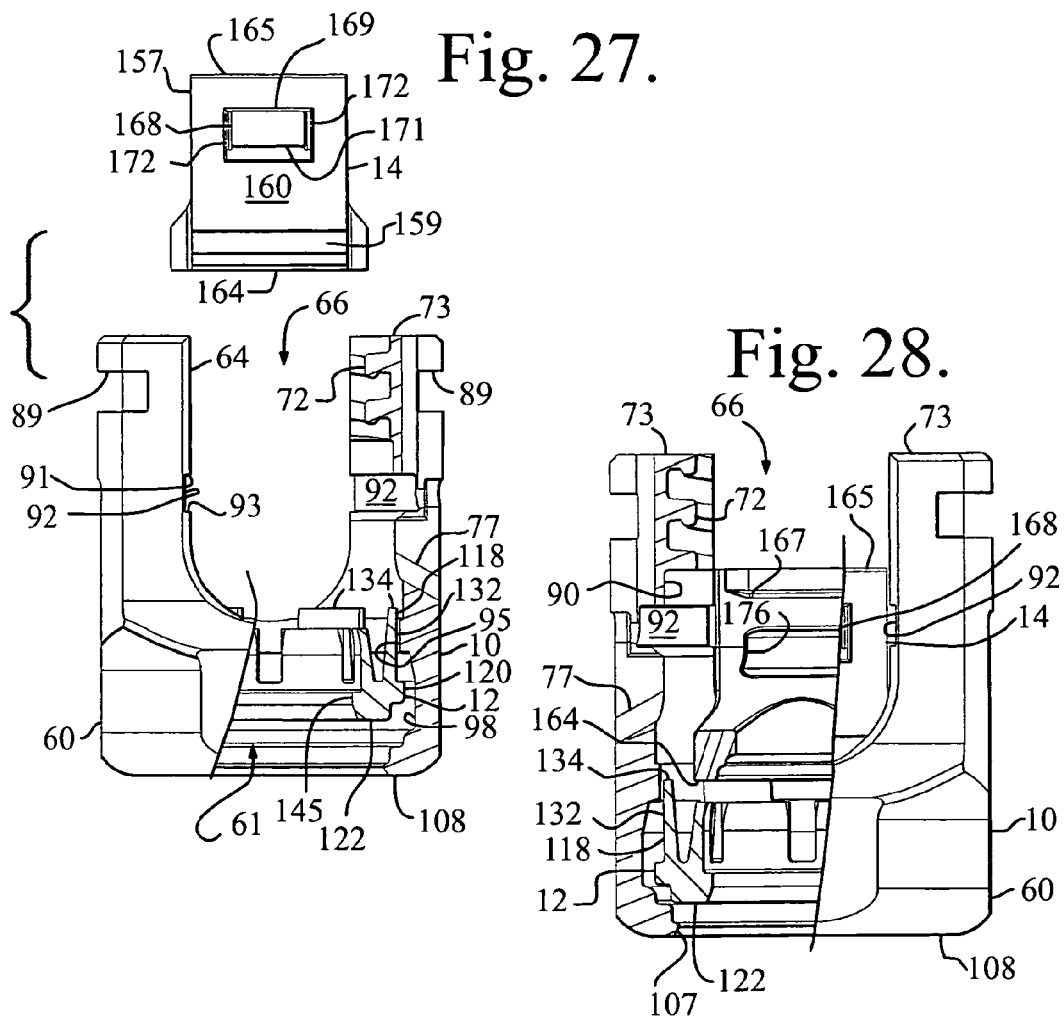
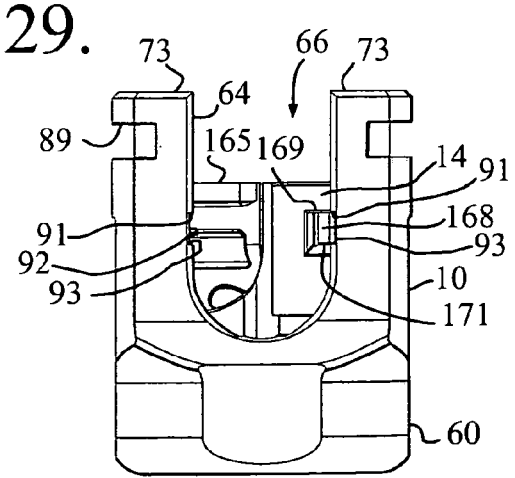

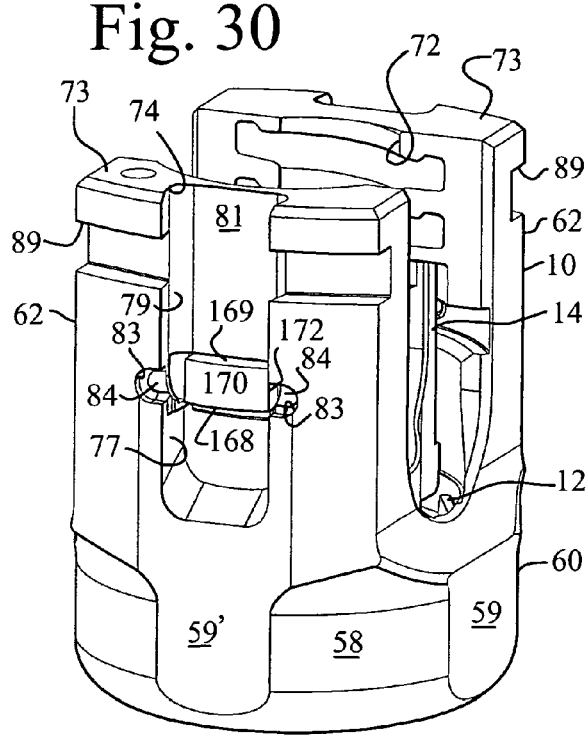

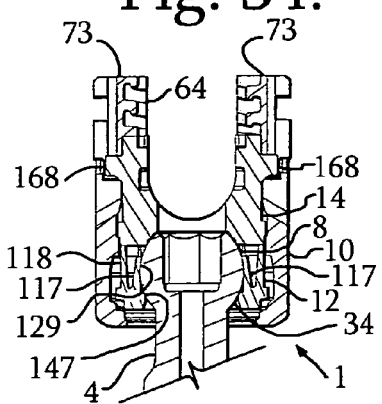
Fig. 34.
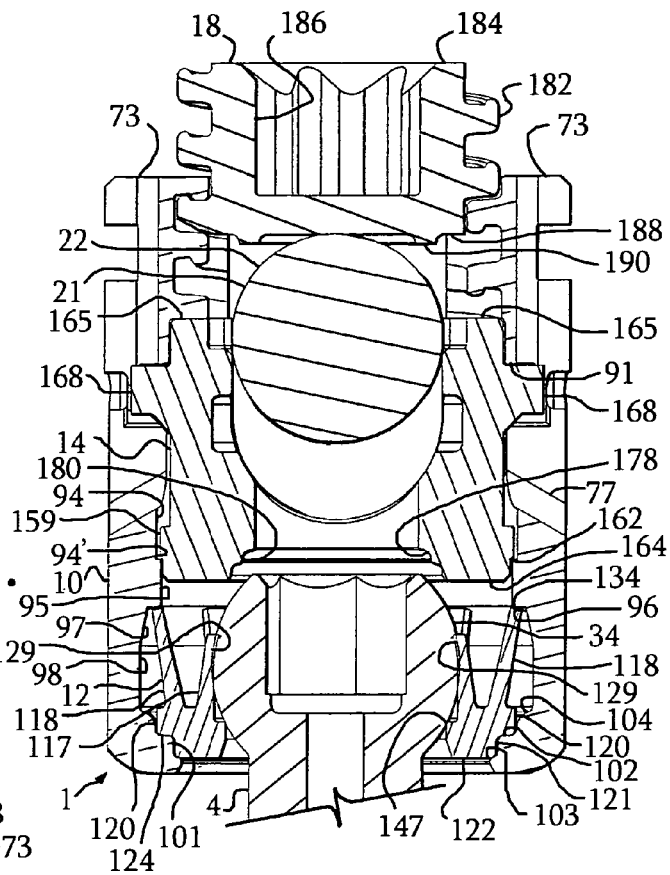
Fig. 35.
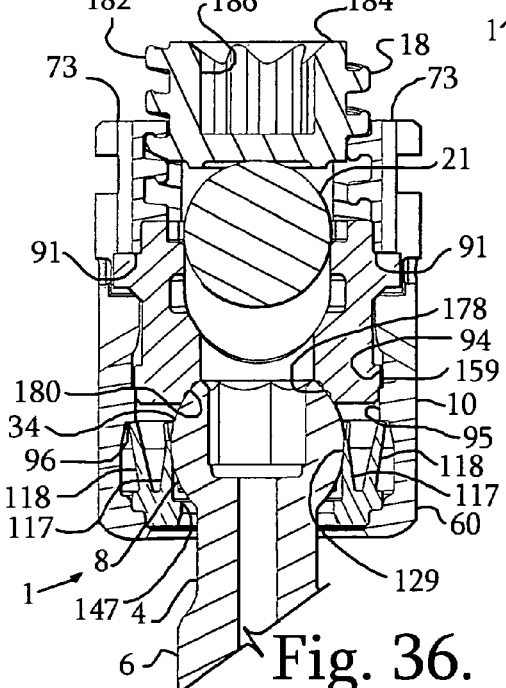
Fig. 36.
Fig. 37.

POLYAXIAL BONE ANCHOR WITH POP-ON SHANK, FRICTION FIT RETAINER, WINGED INSERT AND LOW PROFILE EDGE LOCK

CROSS REFERENCE TO RELATED APPLICATIONS

This application is a continuation of U.S. patent application Ser. No. 13/573,874, filed Oct. 10, 2012, now U.S. Pat. No. 9,480,517, which claims the benefit of U.S. Provisional Application No. 61/627,374, filed on Oct. 11, 2011, each of which is incorporated by reference in its entirety herein, and for all purposes.

U.S. patent application Ser. No. 13/573,874 is also a continuation-in-part of U.S. patent application Ser. No. 13/573,516 filed Sep. 19, 2012, which claims the benefit of U.S. Provisional Application No. 61/626,250, filed Sep. 23, 2011. U.S. patent application Ser. No. 13/573,874 is also a continuation-in-part of U.S. patent application Ser. No. 13/374,439, filed Dec. 29, 2011, which claims the benefit of U.S. Provisional Application No. 61/460,267, filed Dec. 29, 2010, and U.S. Provisional Application No. 61/463,037, filed Feb. 11, 2011. U.S. patent application Ser. No. 13/573,874 is also a continuation-in-part of U.S. patent application Ser. No. 13/373,289, filed Nov. 9, 2011, which claims the benefit of U.S. Provisional Application No. 61/456,649, filed Nov. 10, 2010, and U.S. Provisional Application No. 61/460,234, filed Dec. 29, 2010. U.S. patent application Ser. No. 13/573,874 is also a continuation-in-part of U.S. patent application Ser. No. 13/136,331, filed Jul. 28, 2011, now abandoned, which claims the benefit of U.S. Provisional Application No. 61/400,504, filed Jul. 29, 2010, and U.S. Provisional Application No. 61/403,915, filed Sep. 23, 2010. U.S. patent application Ser. No. 13/573,874 is also a continuation-in-part of U.S. patent application Ser. No. 13/573,303, filed Sep. 7, 2012, now U.S. Pat. No. 9,393,047, which claims the benefit of U.S. Provisional Application No. 61/573,508, filed Sep. 7, 2011. U.S. patent application Ser. No. 13/573,874 is also a continuation-in-part of U.S. patent application Ser. No. 13/506,365, filed Apr. 13, 2012, now U.S. Pat. No. 8,444,681, which claims the benefit of U.S. Provisional Application No. 61/517,088, filed Apr. 13, 2011. U.S. patent application Ser. No. 13/573,874 is also a continuation-in-part of U.S. patent application Ser. No. 13/385,212 entitled, filed Feb. 8, 2012, now U.S. Pat. No. 9,216,041, which claims the benefit U.S. Provisional Application No. 61/463,037, filed Feb. 11, 2011. Each of the above applications is incorporated by reference in its entirety herein, and for all purposes.

U.S. patent application Ser. No. 13/573,874 is also a continuation-in-part of U.S. patent application Ser. No. 12/924,802, filed Oct. 5, 2010, now U.S. Pat. No. 8,556,938, and which application Ser. No. 12/924,802 claims the benefit of the following U.S. Provisional Patent Applications: U.S. Provisional Application No. 61/278,240, filed Oct. 5, 2009; U.S. Provisional Application No. 61/336,911, filed Jan. 28, 2010; U.S. Provisional Application No. 61/343,737, filed May 3, 2010; U.S. Provisional Application No. 61/395,564, filed May 14, 2010; U.S. Provisional Application No. 61/395,752, filed May 17, 2010; U.S. Provisional Application No. 61/396,390 entitled, filed May 26, 2010; U.S. Provisional Application No. 61/398,807, filed Jul. 1, 2010; U.S. Provisional Application No. 61/400,504, filed Jul. 29, 2010; U.S. ProvisionalApplication No. 61/402,959 entitled, filed Sep. 8, 2010; U.S. Provisional Application No. 61/403,696, filed Sep. 20, 2010; and U.S. Provisional Application No. 61/403,915, filed Sep. 23, 2010. Each of the above applications is incorporated by reference in its entirety herein, and for all purposes.

U.S. patent application Ser. No. 13/573,874 is also a continuation-in-part of U.S. patent application Ser. No. 12/802,849, filed Jun. 15, 2010, and which application Ser. No. 12/802,849 claims the benefit of the following U.S. Provisional Patent Applications: U.S. Provisional Application No. 61/268,708, filed Jun. 15, 2009; U.S. Provisional Application No. 61/270,754, filed Jul. 13, 2009; U.S. Provisional Application No. 61/336,911, filed Jan. 28, 2010; U.S. Provisional Application No. 61/395,564, filed May 14, 2010; U.S. Provisional Application No. 61/395,752, filed May 17, 2010; and U.S. Provisional Application No. 61/396,390, filed May 26, 2010. Each of the above applications is incorporated by reference in its entirety herein, and for all purposes.

BACKGROUND OF THE INVENTION

The present invention is directed to polyaxial bone screws for use in bone surgery, particularly spinal surgery and particularly to such screws with compression or pressure inserts and expansion lock split retainers to snap over, capture and retain the bone screw shank head in the receiver member assembly and later fix the bone screw shank with respect to the receiver assembly.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Open-ended polyaxial bone screws typically allow for a loose or floppy rotation of the head or receiver about the shank until a desired rotational position of the receiver is achieved by fixing such position relative to the shank during a final stage of a medical procedure when a rod or other longitudinal connecting member is inserted into the receiver, followed by a locking screw or other closure. This floppy feature can be, in some cases, undesirable and make the procedure more difficult. Also, it is often desirable to insert the bone screw shank separate from the receiver or head due to its bulk which can get in the way of what the surgeon needs to do. Such screws that allow for this capability are sometimes referred to as modular polyaxial screws.

With specific reference to modular snap-on or pop-on polyaxial pedicle screw systems having shank receiver assemblies, the prior art has shown and taught the concept of the receiver and certain retainer parts forming an assembly wherein a contractile locking engagement between the parts is created to fix the shank head with respect to the receiver and retainer. The receiver and shank head retainer assemblies in the prior art have included a slotted contractile retainer ring and/or a lower pressure slotted insert with an expansion and contraction collet-type of structure having contractile locking engagement for the shank head due to direct contact between the retainer and/or the collet structure with the receiver resulting in contraction of the slotted retainer ring and/or the collet-type structure of the insert against the shank head. The receiver and slotted insert have generally included tapered locking engagement surfaces.

The prior art for modular polyaxial screw assemblies has also shown and taught that the contact surfaces on the outside of the slotted collet and/or retainer and the inside of the receiver, in addition to being tapered, can be conical, radiused, spherical, curvate, multi-curvate, rounded, as well as other configurations to create a contractile type of locking engagement for the shank head with respect to the receiver.

In addition, the prior art for modular polyaxial screw assemblies has shown and taught that the shank head can both enter and escape from a collet-like structure on the insert or from the retainer when the insert or retainer is in the up position and within an expansion recess or chamber of the receiver. This is the case unless the slotted insert and/or the slotted retainer are blocked or constrained from being able to be pushed or manipulated back up into the receiver bore or cavity, or unless the screw assemblies are otherwise uniquely configured to prevent this from happening.

SUMMARY OF THE INVENTION

The present invention differentiates from the prior art by not allowing the receiver to be removed from the shank head once the parts are snapped-on and connected. This is true even if the retainer can go back up into the expansion chamber. This approach or design has been found to be more secure and to provide more resistance to pull-out forces compared to the prior art for modular polyaxial screw designs. Collect-like structures extending downwardly from lower pressure inserts, when used in modular polyaxial screw designs, as shown in the prior art, have been found to be somewhat weak with respect to pull-out forces encountered during some spinal reduction procedures.

Embodiments of the present invention also differentiate from the prior art by providing a split retainer ring with inner friction fit surfaces that may be partially radiused that do not participate in the final locking engagement for the shank head with respect to the receiver. In addition, the retainer ring itself is uniquely characterized by a base portion providing expansion to receive and capture the shank head and then having expansion (not contraction) locking engagement between the shank head and the retainer ring base and between the retainer ring base and horizontal and vertical loading surfaces near a bottom opening of the receiver.

The expansion-only retainer ring base portion is positioned entirely below the shank head hemisphere in the receiver and can be a stronger, more substantial structure to resist larger pull out forces on the assembly. The retainer ring base can also be better supported on a generally horizontal loading surface near the lower opening in the bottom of the receiver. This design has been found to be stronger and more secure when compared to that of the prior art which uses some type of contractile locking engagement between the parts, as described above; and, again, once assembled it cannot be disassembled.

Thus, an embodiment of a polyaxial bone screw assembly according to the invention includes a shank having an integral upper portion or integral radiused or spherical head and a body for fixation to a bone; a separate receiver defining an upper open channel, a central bore, a lower cavity and a lower opening; a top drop and turn in place lower compression insert; and a friction fit resilient expansion locking split retainer for capturing the shank head in the receiver lower cavity, the shank head being frictionally engaged with, but still movable in a non-floppy manner with respect to the friction fit retainer and the receiver prior to locking of the shank into a desired configuration. The shank is finally locked into a fixed position relative to the receiver by frictional engagement between the insert and a lower split ring-like portion of the retainer, as described previously, due to a downward force placed on the compression insert by a closure top pressing on a rod, or other longitudinal connecting member, captured within the receiver bore and channel. In the illustrated embodiments, retainers and compression inserts are downloaded into the receiver, but uploaded embodiments are also foreseen. The shank head can be positioned into the receiver lower cavity at the lower opening thereof prior to or after insertion of the shank into bone. In some embodiments, the compression insert may include a lock and release feature for independent locking of the polyaxial mechanism so the screw can be used like a fixed monoaxial screw. Also, in some embodiments, the shank (as well as other components of the assembly, including the closure top) can be cannulated for minimally invasive surgery applications. The retainer includes upwardly extending tangs that are deployed in the receiver cavity so that the retainer and captured shank head are stabilized and retained in the region of the receiver locking chamber once, but are free to rotate within the cavity. In this way, the shank head and retainer are partially constrained and cannot go back up into the receiver cavity, but can be manipulated there-within.

Again, a pre-assembled receiver, compression insert and friction fit split retainer may be "pushed-on", "snapped-on" or "popped-on" to the shank head prior to or after implantation of the shank into a vertebra. Such a "snapping on" procedure includes the steps of uploading the shank head into the receiver lower opening, the shank head pressing against the base portion of the split retainer ring and expanding the resilient lower open retainer portion out into an expansion portion or chamber of the receiver cavity followed by an elastic return of the retainer back to a nominal or near nominal shape thereof after the hemisphere of the shank head or upper portion passes through the lower ring-like portion of the retainer. The shank head enters into friction fit engagement with portions of the retainer, defined at least in part, by inner tangs of the retainer. The retainer snapping onto the shank head as the retainer returns to a neutral or close to neutral orientation, providing a non-floppy connection between the retainer and the shank head. In the illustrated embodiments, when the shank is ultimately locked between the compression insert and the lower portion of the retainer, at least one lower, inner retainer edge surface locks against the shank head. The final fixation occurs as a result of a locking expansion-type of contact between the shank head and the lower edge portion of the split retainer and an expansion-type of non-tapered locking engagement between the lower portion of the retainer ring and the locking chamber in the lower portion of the receiver cavity. The retainer can expand more in the upper portion or expansion chamber of the receiver cavity to allow the shank head to pass through, but has restricted expansion to retain the shank head when the retainer lower ring portion is against the locking chamber surfaces in the lower portion of the receiver cavity and the shank head is forced down against the retainer ring during final locking. In some embodiments, when the polyaxial mechanism is locked, the pressure or compression insert is forced or wedged against a surface of the receiver resulting in an interference locking engagement, allowing for adjustment or removal of the rod or other connecting member without loss of a desired angular relationship between the shank and the receiver. This independent locking feature allows the polyaxial screw to function like a fixed monoaxial screw.

The lower pressure insert may also be configured to be independently locked by a tool or instrument, thereby allowing the pop-on polyaxial screw to be distracted, compressed and/or rotated along and around the rod to provide for improved spinal correction techniques. Such a tool engages the receiver from the sides and then engages outwardly extending winged arms of the insert to force or wedge the insert down into a locked position within the receiver. With the tool still in place and the correction maintained, the rod is then locked within the receiver channel by a closure top followed by removal of the tool. This process may involve multiple screws all being manipulated simultaneously with multiple tools to achieve the desired correction.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a polyaxial bone screw assembly of an embodiment according to the present invention including a shank, a receiver, an open friction fit retainer and a top drop and turn in place lower compression insert, further shown with a portion of a longitudinal connecting member in the form of a rod and a closure top.

FIG. 2 is an enlarged top plan view of the shank of FIG. 1.

FIG. 3 is a reduced cross-sectional view taken along the line 3-3 of FIG. 2.

FIG. 17 is an enlarged perspective view of the insert of FIG. 1.

FIG. 18 is a side elevational view of the insert of FIG. 17.

FIG. 19 is another perspective view of the insert of FIG. 17.

FIG. 20 is a top plan view of the insert of FIG. 17.

FIG. 21 is a bottom plan view of the insert of FIG. 17.

FIG. 27 is an enlarged front elevational view of the retainer and receiver with portions broken away, similar to what is shown in FIG. 25, showing the retainer positioned lower in the receiver cavity and further shows the inert in position for assembly with the receiver.

FIG. 28 is an enlarged front elevational view of the retainer, receiver and insert with portions broken away, similar to what is shown in FIG. 27, further showing the insert being downloaded into the receiver to a location suitable for rotation within the receiver.

FIG. 29 is a reduced front elevational view of the retainer, receiver and insert, similar to what is shown in FIG. 28, further showing the insert being partially rotated within the receiver.

FIG. 30 is an enlarged perspective view of the retainer, receiver and insert of FIG. 29, showing the insert rotated into a desired position for assembly with the shank of FIG. 1 and showing the receiver crimped against the insert.

FIG. 31 is a reduced front elevational view of the assembly of FIG. 30, the figure further showing the shank of FIG. 1 in a partial front elevational view and implanted into a portion of a vertebra, a hemisphere of the shank head and the vertebra portion are both shown in phantom.

FIG. 32 is an enlarged and partial front elevational view with portions broken away, similar to FIG. 31, and further showing the shank in a first stage of assembly with the receiver and retainer.

FIG. 33 is an enlarged and partial front elevational view with portions broken away, similar to FIG. 32, showing the retainer lower portion in an expanded state about a midportion of the shank head.

FIG. 34 is a reduced and partial front elevational view with portions broken away, similar to FIG. 33, the spherical shank upper portion or head shown fully captured by the retainer.

FIG. 35 is an enlarged and partial front elevational view with portions broken away, similar to FIG. 34, the shank upper portion with attached retainer being shown pulled down into a seated position within the lower receiver cavity, the retainer spring tabs in a substantially neutral state, extending outwardly and captured beneath a surface of the receiver, further shown is the rod and closure top of FIG. 1, also shown in an enlarged and partial front elevational view with portions broken away to show the detail thereof.

FIG. 36 is a reduced and partial front elevational view with portions broken away, similar to FIG. 35, the shank being shown in a maximum possible push upped position prior to locking with the rod and closure top.

FIG. 37 is a reduced and partial front elevational view with portions broken away, similar to FIG. 35, the insert being shown pushed down into a fully seated position within the lower receiver cavity by pressure being placed thereon from above by the rod and closure top, the insert being placed in locking interference fit with the receiver.

DETAILED DESCRIPTION OF THE INVENTION

Figure 4:
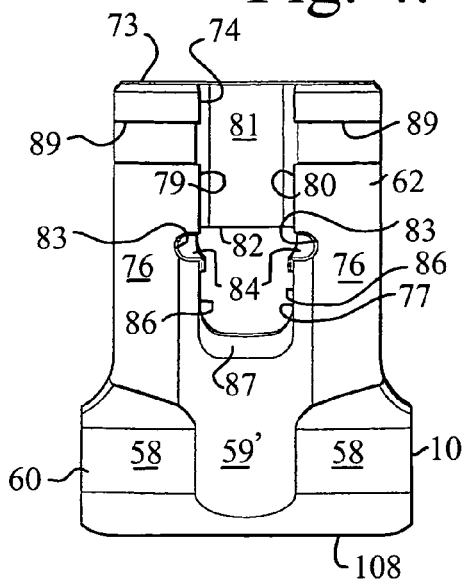
FIG. 4 is an enlarged side elevational view of the receiver of FIG. 1.
Figure 5:
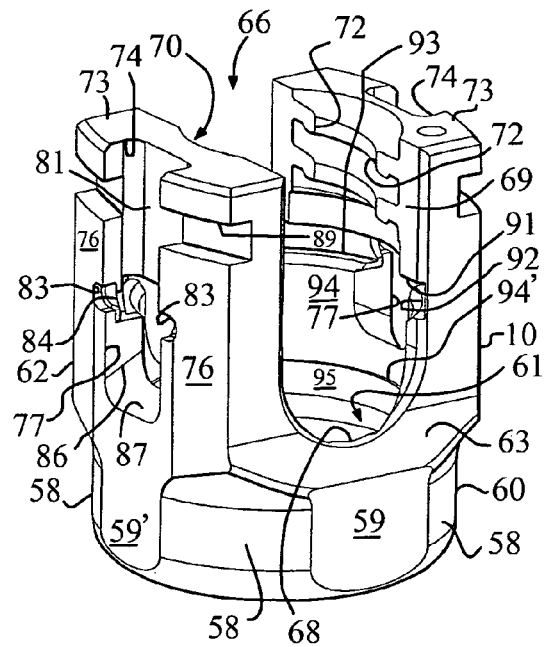
FIG. 5 is a perspective view of the receiver of FIG. 4.
Figure 6:
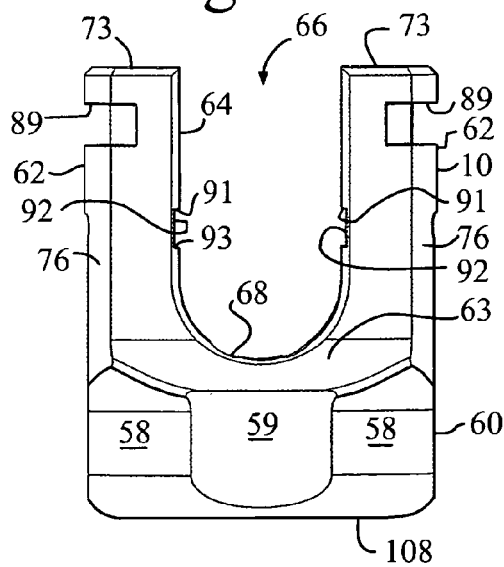
FIG. 6 is a front elevational view of the receiver of FIG. 4.
Figure 7:
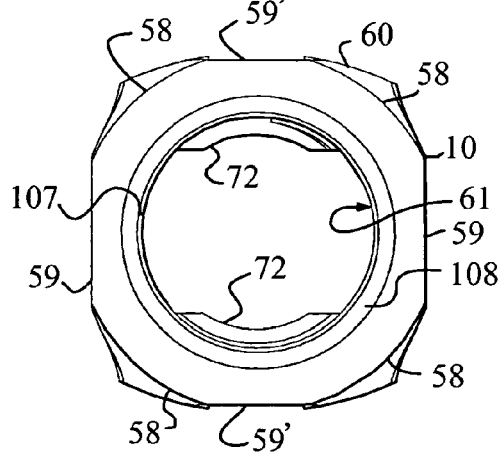
FIG. 7 is a bottom plan view of the receiver of FIG. 4.
Figure 8:
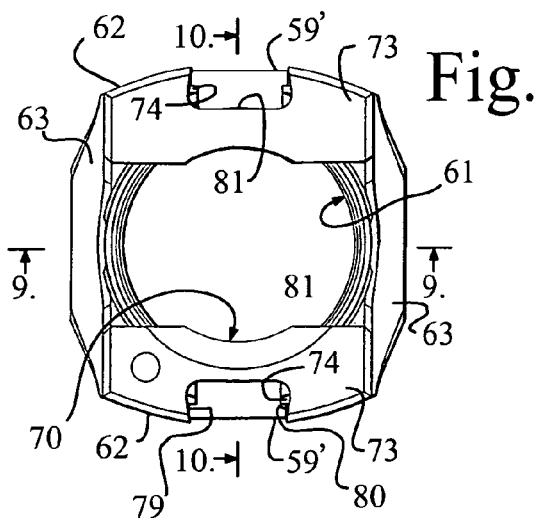
FIG. 8 is a top plan view of the receiver of FIG. 4.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

With reference to FIGS. 1-45, the reference number 1 generally represents an embodiment of a polyaxial bone screw apparatus or assembly according to the present invention. The assembly 1 includes a shank 4, that further includes a body 6 integral with an upwardly extending upper portion or head 8; a receiver 10; a friction fit retainer 12, and a crown-like compression or pressure insert 14. The receiver 10, retainer 12 and compression insert 14 are initially assembled and may be further assembled with the shank 4 either prior or subsequent to implantation of the shank body 6 into a vertebra 17, as will be described in greater detail below. FIGS. 1 and 35-37 further show a closure structure 18 for capturing a longitudinal connecting member, for example, a rod 21 which in turn engages the compression insert 14 that presses against the shank head 8 into fixed frictional contact with the retainer 12, so as to capture, and fix the longitudinal connecting member 21 within the receiver 10 and thus fix the member 21 relative to the vertebra 17. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. The illustrated rod 21 is hard, stiff, non-elastic and cylindrical, having an outer cylindrical surface 22. In some embodiments, the rod 21 may be elastic, deformable and/or of different materials and cross-sectional geometries (see, e.g., FIGS. 38 and 39). As shown in FIG. 39, in some embodiments of the invention, the closure top presses directly on the insert 14, for example, when the rod is deformable.

The shank 4, best illustrated in FIGS. 1-3, is elongate, with the shank body 6 having a helically wound bone implantable thread 24 (single or dual lead thread form and different thread types) extending from near a neck 26 located adjacent to the upper portion or head 8, to a tip 28 of the body 6 and extending radially outwardly therefrom. During use, the body 6 utilizing the thread 24 for gripping and advancement is implanted into the vertebra 17 leading with the tip 28 and driven down into the vertebra with an installation or driving tool (not shown), so as to be implanted in the vertebra to a location at or near the neck 26, as shown in FIG. 31, for example, and more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion or head 8 that provides a connective or capture apparatus disposed at a distance from the upper end 32 and thus at a distance from the vertebra 17 when the body 6 is implanted in such vertebra.

The shank upper portion 8 is configured for a pivotable connection between the shank 4 and the retainer 12 and receiver 10 prior to fixing of the shank 4 in a desired position with respect to the receiver 10. The shank upper portion 8 has an outer, convex and substantially spherical surface 34 that extends outwardly and upwardly from the neck 26 that terminates at a substantially annular, planar rim surface 38 that is perpendicular to the shank central axis A. In some embodiments, a frusto-conical surface extends from the spherical surface 34 inwardly to the top surface 38, providing additional clearance during pivoting of the shank with respect to the receiver 10 and the insert 14. The spherical surface 34 has an outer radius configured for temporary frictional, non-floppy, sliding cooperation with one or more edges and/or surfaces of the retainer 12, as well as ultimate frictional engagement with the retainer 12 at, at least one lower inner edge thereof and ultimate frictional engagement with the insert 14 at an inner partially spherical surface thereof and/or stepped or ridged surfaces thereof, as will be discussed more fully in the paragraphs below. In FIG. 1 and some of the other figures, a dotted line 40 designates a hemisphere of the spherical surface 34. The spherical surface 34 shown in the present embodiment is substantially smooth, but in some embodiments may include a roughening or other surface treatment and is sized and shaped for cooperation and ultimate frictional engagement with the compression insert 14 as well as ultimate frictional engagement with a lower ring-like edge of the retainer 12. The shank spherical surface 34 is locked into place exclusively by the insert 14 and the retainer 12 lower edged portion and not by inner surfaces defining the receiver cavity.

A counter sunk and stepped or graduated annular seating surface or base 45 partially defines a portion of an internal drive feature or imprint 46. In some embodiments of the invention, the surface 45 is substantially planar. The illustrated internal drive feature 46 is an aperture formed in the top 38 and has a hex shape designed to receive a tool (not shown) of an Allen wrench type, into the aperture for rotating and driving the bone screw shank 4 into the vertebra 17. It is foreseen that such an internal tool engagement structure may take a variety of tool-engaging forms and may include one or more apertures of various shapes, such as a pair of spaced apart apertures or a multi-lobular or star-shaped aperture. The graduated seat or base surfaces 45 of the drive feature 46 are disposed substantially perpendicular to the axis A with the drive feature 46 otherwise being coaxial with the axis A. As illustrated in FIGS. 2 and 3, the drive seat 45 having beveled or stepped surfaces advantageously further enhances gripping with the driving tool. In operation, the driving tool (not shown) is received in the internal drive feature 46, being seated at the base 45 and engaging the faces of the drive feature 46 for both driving and rotating the shank body 6 into the vertebra 17, either before or after the shank 4 is connected to the receiver 10 via the retainer 12, the driving tool extending into the receiver 10 when the shank 4, retainer 12 and receiver 10 combination is driven into the vertebra 17.

The shank 4 shown in the drawings is cannulated, having a small central bore 50 extending an entire length of the shank 4 along the axis A. The bore 50 is defined by an inner cylindrical wall of the shank 4 and has a circular opening at the shank tip 28 and an upper circular opening communicating with the external drive 46 at the driving seat 45. The bore 50 is coaxial with the threaded body 6 and the upper portion or head 8. The bore 50 provides a passage through the shank 4 interior for a length of wire (not shown) inserted into the vertebra 17 prior to the insertion of the shank body 6, the wire providing a guide for insertion of the shank body 6 into the vertebra 17. It is foreseen that the shank could be solid and made of different materials, including metal and non-metals.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 4-10, the receiver 10 has a generally U-shaped appearance with partially discontinuous cylindrical inner and outer profiles as well as planar and other curved surfaces. The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 17, the axis B is typically disposed at an angle with respect to the axis A, as shown, for example, in FIGS. 40-45.

The receiver 10 includes a base 60 with various curved surfaces 58, opposed outer planar surfaces 59, and opposed outer planar surfaces 59', the base 60 defining a bore or inner cavity, generally 61, the base 60 being integral with a pair of opposed upstanding arms 62. At the base 60, the planar surfaces 59 are located between the arms 62 and an inset surface portion 63 is located above and adjacent to each planar surface 59, each inset surface portion 63 spanning between the pair of arms 62. The arms 62 form a cradle and define a U-shaped channel 64 between the arms 62 with an upper opening, generally 66, and a U-shaped lower channel portion or seat 68, the channel 64 having a width for operably snugly receiving the rod 21 or portion of another longitudinal connector (or sleeve of a tensioned cord connecting member) between the arms 62, the channel 64 communicating with the base cavity 61. Inner opposed substantially planar arm surfaces 69 partially define the channel 64 above the curved seat 68 and partially define outer sides of each arm interior surface generally 70, that includes various inner cylindrical profiles, an upper one of which is a partial helically wound guide and advancement structure 72 located adjacent top surfaces 73 of each of the arms 62. In the illustrated embodiment, the guide and advancement structure 72 is a partial helically wound interlocking flangeform configured to mate under rotation with a similar structure on the closure structure 18, as described more fully below. However, it is foreseen that for certain embodiments of the invention, the guide and advancement structure 72 could alternatively be a square-shaped thread, a buttress thread, a reverse angle thread or other thread-like or non-thread-like helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms 62 could have break-off extensions.

An opposed pair of vertically extending outer grooves, generally 74, running substantially parallel to the receiver axis B are centrally formed in outer curved convex surfaces 76 of the arms 62. Each groove 74 runs centrally from the respective arm top surface 73 and terminates at a a lower through aperture 77. Each aperture 77 extends through the respective arm surface 77 to the respective inner arm surface 70 and is located spaced from the receiver base 60. Each groove 74 has an upper opening partially defined by a pair of opposed surfaces 79 and 80 and a substantially planar outer wall surface 81 extending between the surfaces 79 and 80. The planar wall surface terminates at the top arm surface 73 and at a lower surface 82 partially defining the aperture 77. The opposed surfaces 79 and 80 are disposed at a slight angle with respect to each other, forming the groove 74 as a dovetail-like space for easily receiving an elongate tool (not shown) that enters into the groove 74 at the arm top surface 73 and is kept in close sliding contact with the surface 81 by the orientation of the surfaces 79 and 80 angling toward one another with the tool sliding along the surface 81 and ultimately into contact with winged portions of the insert 14 that extend through the aperture 77 as will be described in greater detail below. At the through aperture 77, the dovetail surfaces 79 and 80 terminate near facing generally c-shaped ears 83 that do not extend completely through the respective arm 62, but rather include a thin wall that provides a crimping portion or wall 84. The crimping portions or walls 84 are sized and shaped for pressing or crimping some or all of the wall material into grooves or arms surfaces adjacent to the wings of the insert 14 to prohibit rotation and misalignment of the insert 14 with respect to the receiver 10 as will be described in greater detail below. In other embodiments of the invention, other surfaces at or near the grooves 74 may be inwardly crimped. The illustrated through aperture 77 located below each grooves 74 is substantially the same width as the groove 74 there-above, each aperture 77 being partially defined by a pair of opposed side walls 86 and a bottom surface 87, resulting in the aperture 77 having a substantially rectangular profile. Each surface 87 slants outwardly and downwardly from the inner arm surface 70 toward the receiver base 60 outer planar surface 59'. The through apertures 77 are sized and shaped for receiving tooling and also the outer tangs of the retainer 12 during assembly as shown, for example, in FIG. 24.

The receiver 10 is a one-piece or integral structure and is devoid of any spring tabs or collet-like structures. Preferably the insert and/or receiver are configured with structure for blocking rotation of the insert with respect to the receiver, such as the crimp walls 84, but allowing some up and down movement of the insert with respect to the receiver during the assembly and implant procedure. Also formed in each outer arm surface 76 near the top surface 73 is an undercut tool receiving and engaging groove 89. Some or all of the apertures and grooves described herein, including, but not limited to grooves 74, apertures 77, and grooves 89 may be used for holding the receiver 10 during assembly with the insert 14, the retainer 12 and the shank 4; during the implantation of the shank body 6 into a vertebra when the shank is pre-assembled with the receiver 10; during assembly of the bone anchor assembly 1 with the rod 21 and the closure structure 18; and during lock and release adjustment of insert embodiments according to the invention with respect to the receiver 10, either into or out of frictional engagement with the inner surfaces of the receiver 10 as will be described in greater detail below. It is foreseen that tool receiving grooves or apertures may be configured in a variety of shapes and sizes and be disposed at other locations on the receiver arm 62 outer surfaces 76 and/or inner surfaces 70 as well as the base 60 outer or inner surfaces.

Figure 9:
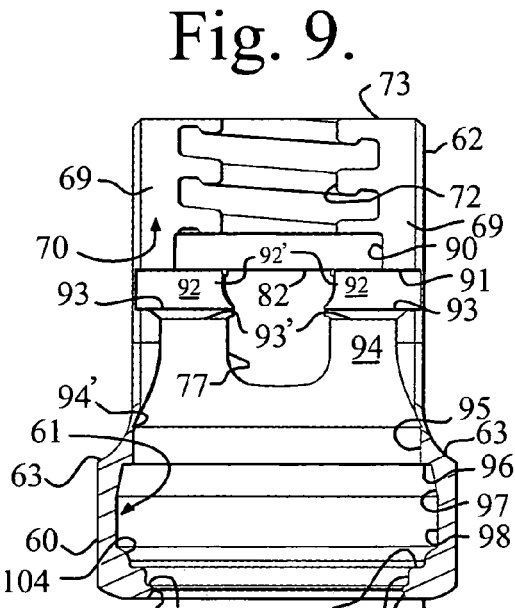
FIG. 9 is a cross-sectional view taken along the line 9-9 of FIG. 8.
Figure 10:
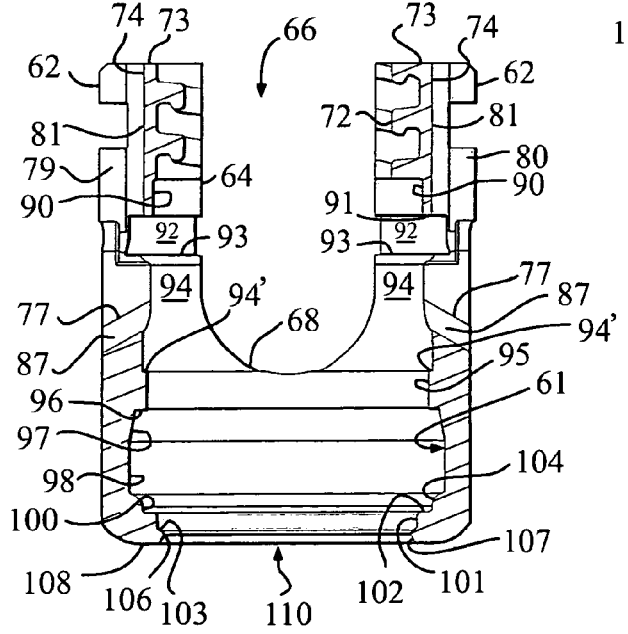
FIG. 10 is a cross-sectional view taken along the line 10-10 of FIG. 8.
Figure 11:
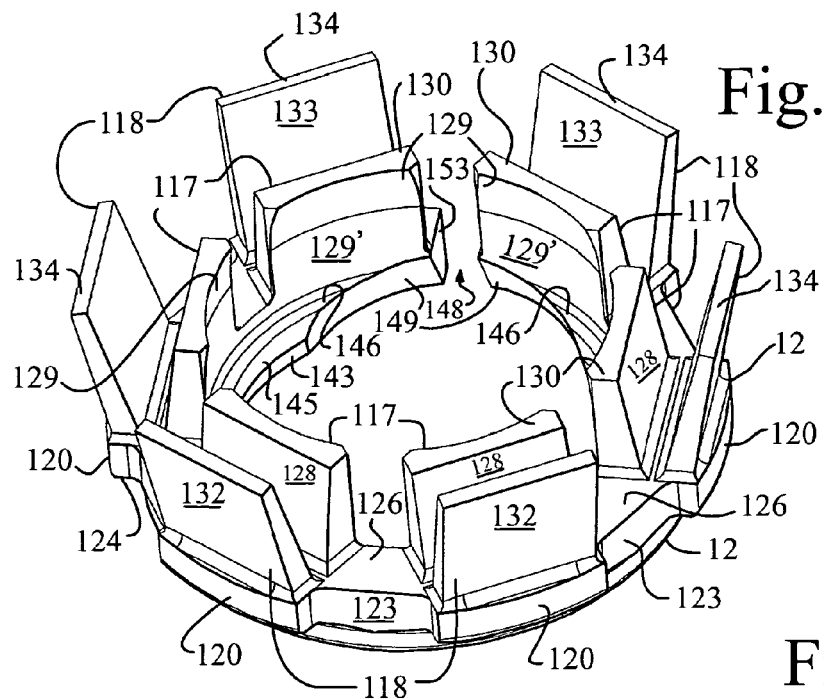
FIG. 11 is an enlarged perspective view of the retainer of FIG. 1.
Figure 12:
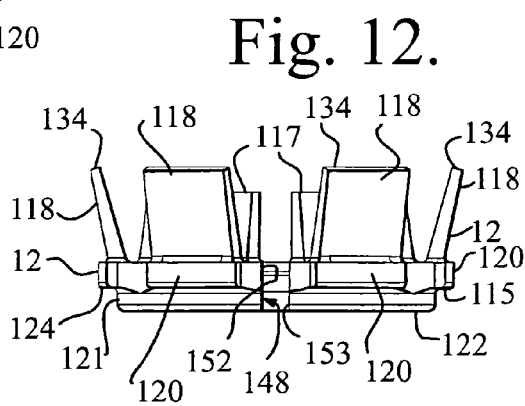
FIG. 12 is a reduced front elevational view of the retainer of FIG. 11.
Figure 13:
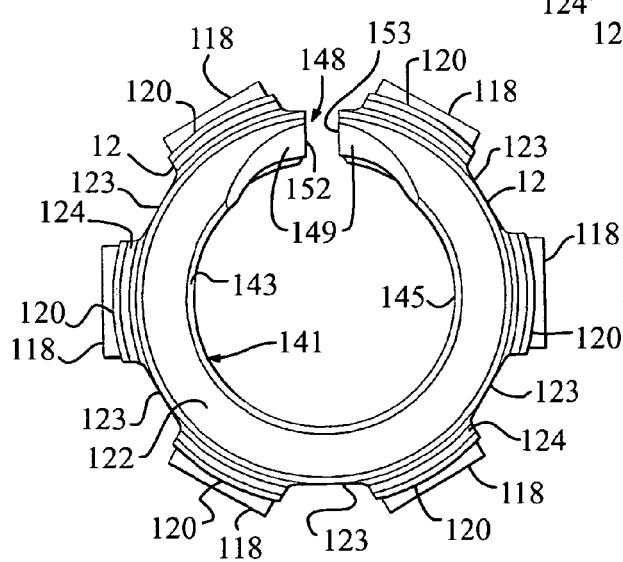
FIG. 13 is a reduced bottom plan view of the retainer of FIG. 11.
Figure 14:
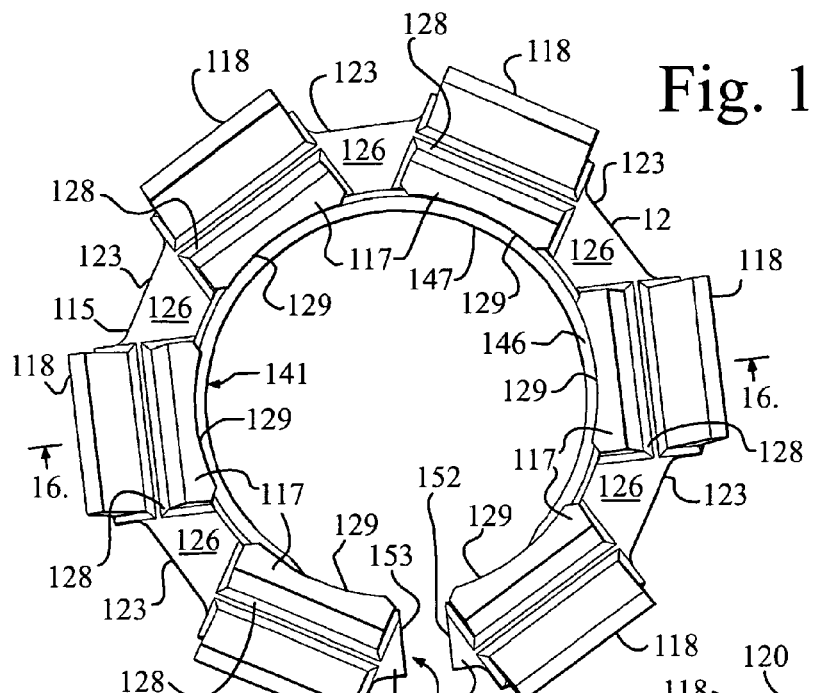
FIG. 14 is a top view of the retainer of FIG. 11.
Figure 15:
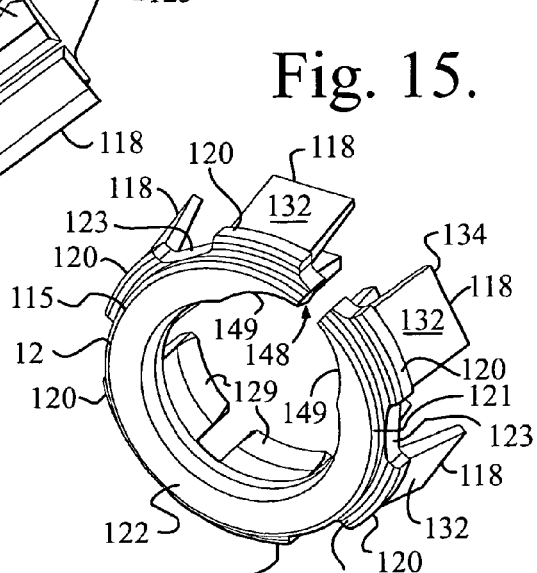
FIG. 15 is a reduced bottom perspective view of the retainer of FIG. 11.
Figure 16:
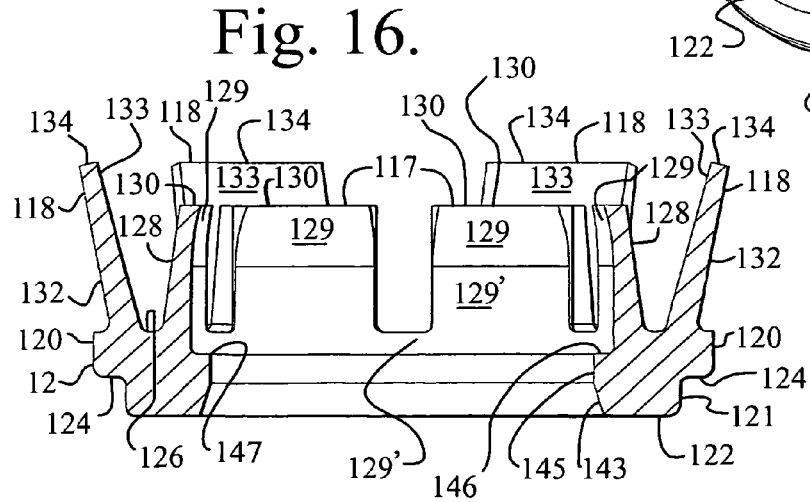
FIG. 16 is an enlarged cross-sectional view taken along the line 16-16 of FIG. 14.
Figure 22:
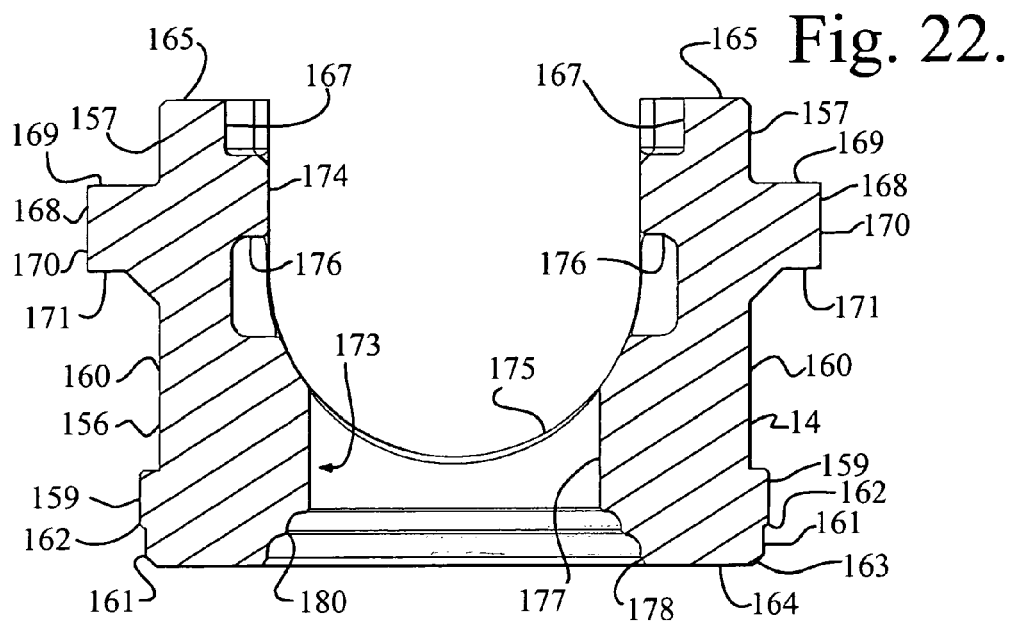
FIG. 22 is an enlarged cross-sectional view taken along the line 22-22 of FIG. 20.
Figure 23:
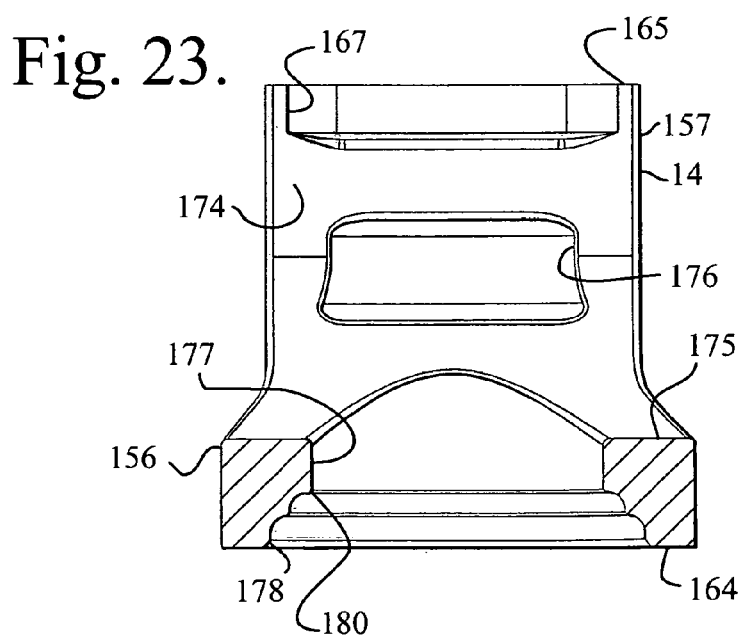
FIG. 23 is an enlarged cross-sectional view taken along the line 23-23 of FIG. 20.

Returning to the interior surface 70 of the receiver arms 62, located below the guide and advancement structure 72 is a discontinuous cylindrical surface 90 partially defining a run-out feature for the guide and advancement structure 72. Adjacent the surface 90 is a ledge or upper annular surface 91 that in turn is adjacent to another cylindrical surface 92 having a larger diameter than the cylindrical surface 90. As best shown in FIG. 9, the upper annular surface 91 includes the upper surface 82 that partially defines the aperture 77. The cylindrical surface 92 is sized and shaped to receive an upper winged portion of the insert 14 as will be described in greater detail below. Therefore, the surface 92 has a diameter greater than a greater diameter of the guide and advancement structure 72. The receiver 10 may further includes sloped, stepped or chamfered surfaces above and below the surface 92. The surface 92 is divided not only by the U-shaped channel 64, but also by each of the through apertures 77, resulting in the surface 92 being in four sections. At each aperture 77, the surface 92 includes a surface portion 92' that is located at the inside of ears 83 of the crimping wall portions 84, the surface portions 92' eventually in contact with the insert 14 as will be described below. A lower, substantially annular ledge 93 faces each upper ledge or annular surface 91 and is adjacent the cylindrical surface 92. An inwardly and downwardly sloping surface or chamfer 93' is adjacent to each surface 93 and also adjacent to another discontinuous cylindrical arm surface 94. Each cylindrical surface 94 has a diameter smaller than the surface 92 and extends all the way down to the U-shaped channel seat 68. A portion of each aperture 77 extends through each surface 94. A lower partially sloping or stepped ledge 94' at the base of the cylindrical surface 92 slopes downwardly toward the receiver base 60 and extends inwardly toward the axis B, the surface 94 terminating at a cylindrical surface 95 that extends completely around the receiver base 60 and thus runs beneath each arm 62 and is adjacent to the lower seat 68. The inner surface 95 thus defines an upper and inner portion of the receiver base 60. The cylindrical surface has a diameter slightly smaller than the diameter of the surface 94. The surface 95 terminates at a ledge surface or chamber ceiling 96 that extends outwardly away from the axis B, the surface 96 being substantially perpendicular to the axis B, but could be oblique. The surface 96 is annular and defines an upper ceiling or stop of a retainer ring expansion portion or chamber of the inner cavity 61 that is further defined by an adjacent outwardly sloping surface 97 and a cylindrical surface 98 that is adjacent the surface 97. The surface 97 also acts as a stop for and slidingly cooperates with outwardly and upwardly projecting retainer tangs or panels as will be described in greater detail below. The cylindrical surface 98 has a diameter greater than the diameter of the cylindrical surface 95. The cylindrical surfaces 92, 95 and 98 are all centrally aligned with and run parallel to the receiver axis B. The surface 98 defines a circumferential recess that is sized and shaped to receive the retainer 12 as it expands around the shank upper portion 8 as the shank 8 moves upwardly toward the channel 64 during assembly. It is foreseen that the recess could be tapered or conical in configuration.

A pair of cylindrical surfaces 100 and 101 with an annular step surface 102 therebetween as well as a lower annular step 103 located below and adjacent to the surface 101 provide a lower seat for the retainer 12 as will be described in greater detail below. The surfaces 102 and 103 are substantially perpendicular to the surfaces 100 and 101 and the receiver axis B. The surfaces 100, 101, 102 and 103 are located below the cylindrical surface 98 in the lower part of the base 60 and are sized and shaped to closely receive and surround a lower base portion and lower skirt or substructure of the retainer 12 when the retainer is in a nominal or reduced deployment position as shown in FIGS. 35-37, for example. Thus, the cylindrical surface 101 has a diameter smaller than the diameter of the cylindrical surface 98 that defines the expansion area or expansion chamber for the retainer 12. The surface 101 is joined or connected to the surface 98 by one or more beveled, curved or conical transition step surfaces 104. The surfaces 104 allow for sliding and nominal or deployment positioning of the retainer 12 into the space defined by the surfaces 100 and 101 and ultimate seating of the retainer 12 on the lower substantially horizontal annular surfaces 102 and 103.

Located below and adjacent to the annular seating surface 103 is a lower edge or rim surface 106 that communicates with a beveled or flared bottom opening surface 107, the surface 107 communicating with an exterior base or bottom surface 108 of the base 60, defining a lower opening, generally 110, into the base cavity 61 of the receiver 10. In some embodiments of the invention, it is foreseen that one or more curvate cut-out or cupped surfaces may be formed in a portion of the base surface 108, as well as in portions of the surfaces 107, 106 and 100-104, typically located substantially centrally and directly below an arm 62. Such a cupped surface may be sized and shaped for providing clearance for an increased angle of articulation between the shank 4 and the receiver 10 (see, e.g., FIG. 55).

With particular reference to FIGS. 1 and 11-16, the lower open or split friction fit retainer 12, that operates to capture the shank upper portion 8 within the receiver 10 is shown. In certain stages of assembly and operation, the retainer 12 is partially constrained within the receiver, being captured within the receiver cavity 61 at a location below the surface 96, the retainer 12 being rotatable with respect to the receiver, but not pivotable thereto and not readily removable out of the receiver once deployed downward into the receiver cavity 61. The retainer 12 has a central axis that is operationally the same as the axis B associated with the receiver 10 when the shank upper portion 8 and the retainer 12 are installed within the receiver 10. The retainer 12 includes a substantially annular, cylindrical discontinuous body 115. Extending upwardly and outwardly from the body 115, and integral thereto, is a super-structure in the form of two sets of flexible panels or tangs, in particular, inner panels or tangs 117 and outer panels or tangs 118, the panels 117 and 118 extending upwardly in aligned pairs, allowing for lateral spaces between the pairs panels or tangs to provide clearance during assembly of the retainer 12 with the receiver 10 inner surfaces (see, e.g., FIGS. 24 and 25). The illustrated embodiment includes six pairs of inner and outer panels or tangs 117, 118, but it is foreseen that more or fewer panels or tangs may be used. The pairs of panels or tangs are generally equally spaced about the body 115. Also integral to the body 115 are six outer discontinuous cylindrical support surfaces 120, each surface 120 located beneath one of the outer panels 118 and extending radially outwardly from the body 115. Below the surfaces 120, the cylindrical body 115 forms a lower outer cylindrical skirt 121 broken only by a gap that will be described in greater detail below. The outer surface 121 is adjacent a bottom surface 122. The body 115 also includes outer surface portions 123 that are located between each outer panels 118 and support surfaces 120. The surface portions 123 are illustrated as substantially planar, but may be cylindrical. At each of the panels 118, a lower ledge surface 124 is adjacent to one of the outer support surfaces 120. Each lower ledge 124 spans between one of the surfaces 120 and the cylindrical skirt surface 121. The lower skirt 121 and the ledge surfaces 124, as well as the surfaces 120 are receiver seating surfaces as will be described in greater detail below. In the illustrated embodiment, transition areas where the body 115 meets the panels 117 and 118 or the retainer bottom 122 are curved or chamfered. Each body portion 123 is adjacent to a substantially planar body top surface 126 that is substantially located between pairs of panels 117 and 118 forming a planar surface with a trapezoidal profile and also includes a narrow strip that runs between the inner panels 117 and the outer panels 118.

The inner panels or tangs 117 each include a substantially planar outer surface 128 and a concave inner surface 129, the surfaces 129 each being partially radiused and partially cylindrical, making up a discontinuous curved surface sized and shaped for friction fit engagement with the shank head 8 as best shown in FIG. 35 and as will be described in greater detail below. However, it is foreseen that the panel inner surfaces 129 may also be planar or include edges or other surfaces features for gripping, but not locking the retainer 12 to the shank head 8 during assembly and manipulation, but prior to locking of the polyaxial mechanism of the bone screw assembly 1. The panels 117 generally slant or curve inwardly towards the central axis of the retainer 12 and thus ultimately inwardly toward the shank head 8. Each panel 117 includes a top surface 130 that is substantially planar and runs substantially parallel to the bottom surface 122 when the retainer is in a neutral position such as that shown in FIG. 16.

The outer panels or tangs 118 each have a planar outer surface 132, a planar inner surface 133 and a planar top surface 134 that slopes at an oblique angle with respect to the retainer bottom surface 122. The surfaces 134 are perpendicular to adjacent surfaces 132. The panels 118 generally extend outwardly away from the panels 117 as well as outwardly and upwardly from the central axis of the retainer body 115. Each surface 133 faces an outer surface 128 of one of the panels 117. The body top surface 126 is reduced to a narrow strip between each pair of panels 117 and 118. The panels or tangs 117 and 118 are resilient, the panels being expandable about the shank head 8 and the panels 118 being compressible inwardly and resiliently holding against the receiver inner surfaces during shipping and certain assembly steps. The panels 118 then return to an original or near original shape within the receiver cavity 61, capturing the retainer 12 within the receiver 10, but still allowing for rotation of the retainer 12 with respect to the receiver 10 about the receiver central axis B.

The retainer ring 12 is made from a resilient material, such as a stainless steel or titanium alloy, so that the retainer 12 body 115 may be expanded and the tabs or panels 117 and 118 of the retainer may be manipulated during various steps of assembly as will be described in greater detail below. The retainer 12 has a central channel or hollow through bore, generally 141, that passes entirely through the retainer 12 from the inner panel top surfaces 130 to the bottom surface 122 of the retainer body 115. Surfaces that define the channel or bore 141 at the body 115 include a discontinuous inner lower frusto-conical surface 143 adjacent to the retainer body bottom surface 122, a discontinuous, substantially cylindrical surface 145 adjacent the frusto-conical surface 143 and a discontinuous annular step 146 located adjacent the cylindrical surface 145, the surface 146 being substantially parallel to the bottom surface 122 and extending between the surface 145 and a lower cylindrical portion 129' of the inner surface 129 that partially forms the inner panels 117. The surfaces 145 and 146 terminate and join together at an edge 147 that is positioned and configured to engage the shank surface 34 as will be described in greater detail below. The inner cylindrical surface 129' adjacent the step 146 forms a continuous inner cylindrical wall except at a slit, generally 148 that runs through the body 115. The slit 148 creates a split or open ring retainer 12, the slit cutting entirely through the retainer body 115. In some embodiments, such a slit may run at an angle obtuse to the bottom surface 122. In the illustrated embodiment, the slit 148 runs substantially perpendicular to the surfaces 122. The slit 148 is primarily for expansion of the retainer 12 during pop-on or snap-on assembly with the shank head 8. However, the slit 148 also compresses during assembly with the receiver 10 as will be described in greater detail below. The slit 148 extends between the body top surface 126 and the bottom surface 122 and is located substantially centrally between two pairs of panels 117 and 118. Furthermore, at the location of the slit 148, a curved concave, cut-out surface 149 is formed in the bottom surface 122 and the frusto-conical surface 143. The cut-out surface 149 also extends into the cylindrical surface 145 and removes a portion of the step 146 at either side of the slit 148. The surface 149 is radiused or otherwise curved for engagement with the shank head 8 at the surface 34 as will be described in greater detail below. In the illustrated embodiment, the cut-out surface 149 is located substantially equally on either side of the slit 148 to provide for a desirable increased angle of orientation between the shank 8 and the retainer 12 and thus a desirable increased or extended angle of articulation between the shank 8 and the receiver 10. The rotatability of the semi-constrained retainer 12 with respect to the receiver 10 allows for manipulation and placement of such an increased angle of articulation to a location desired by a surgeon. The through slit 148 of the resilient retainer 12 is defined by first and second end surfaces, 152 and 153 disposed in substantially parallel spaced relation to one another when the retainer is in a neutral or nominal state. Both end surfaces 152 and 153 are disposed perpendicular to the bottom surface 122, but in some embodiments may be disposed at an obtuse angle thereto. A width between the surfaces 152 and 153 is narrow to provide stability to the retainer 12 during operation, but wide enough to allow for some compression of the retainer during assembly as will be described in greater detail below. Because the retainer 12 is top loadable in a substantially neutral state and ultimately expands during locking of the polyaxial mechanism, the width of the slit 148 may be much smaller than might be required for a bottom loaded compressible retainer ring.

With particular reference to FIGS. 1 and 17-23, the locking compression insert 14 is illustrated that is sized and shaped to be received by and down-loaded into the receiver 10 at the upper opening 66. The compression insert 14 has an operational central axis that is the same as the central axis B of the receiver 10. In operation, the insert advantageously frictionally engages the bone screw shank upper portion 8 as well as engaging the receiver 10 in an interference fit engagement, locking the shank 4 in a desired angular position with respect to the receiver 10 that remains in such locked position even if, for example, a rod and closure top are later removed and the rod is replaced with another rod or other longitudinal connecting member or member component, such as a sleeve of a tensioned cord connecting member. Such locked position may also be released by the surgeon if desired with insert engaging tools (not shown). As will be described in greater detail below with respect to the alternative insert 14" shown in FIGS. 57-59, in some embodiments of the invention, the insert does not have the receiver interference fit feature. The locking insert 14, the non-locking insert 14" and an alternative locking insert 14' for use with a deformable rod (shown in FIGS. 38 and 39) are preferably made from a solid resilient material, such as a stainless steel or titanium alloy, so that portions of the insert may be grasped, pinched or pressed, if necessary, and un-wedged from the receiver 10 with a release tool (not shown).

The locking compression insert 14 includes a body 156 with cylindrical surfaces of a variety of diameters, the body 156 being integral with a pair of upstanding arms 157. Located between the arms 157, the body 156 has an outer partial cylindrical surface 158. Located beneath each upstanding arm 157 is a discontinuous, cylindrical, interference fit surface or band 159 that extends outwardly from an arm and body outer substantially cylindrical surface 160, a diameter of the surface 159 being larger than a diameter of the surface 160. Beneath each surface 159 is a discontinuous cylindrical surface 161 having a diameter the same or similar to the surface 160. A lower ledge surface 162 spans between each surface 159 and the corresponding lower cylindrical surface 161. The lower surface 161 is adjacent to a chamfered surface 163 that is in turn adjacent a substantially planar and annular bottom surface 164.

The insert 14 further includes substantially planar arm top surfaces 165 located opposite the bottom surface 164. Adjacent the top surfaces 165 of the arms 157 are opposed inwardly facing cut-outs or grooved surfaces 167. The arms 157 are sized and configured for ultimate placement at or beneath the cylindrical run-out surface 90 located below the receiver guide and advancement structure 72. The grooves or apertures 167 provide holding surfaces for tools and also provide some clearance between the closure top 18 and the insert 14 when both are within the cylindrical run-out surface 90 of the receiver so that the closure top 18 frictionally engages the rod 21 only, pressing the rod 21 downwardly against the insert 14 that in turn presses against the shank 4 upper portion 8 that presses against the retainer 12 to lock the polyaxial mechanism of the bone screw assembly 1 at a desired angle. Additionally, the grooves 167 may be sized and shaped to cooperate with protrusions or extensions on sleeves that cooperate with a tensioned cord of a longitudinal connecting member assembly to center such a sleeve within the bone screw assembly 1.

Figure 38:
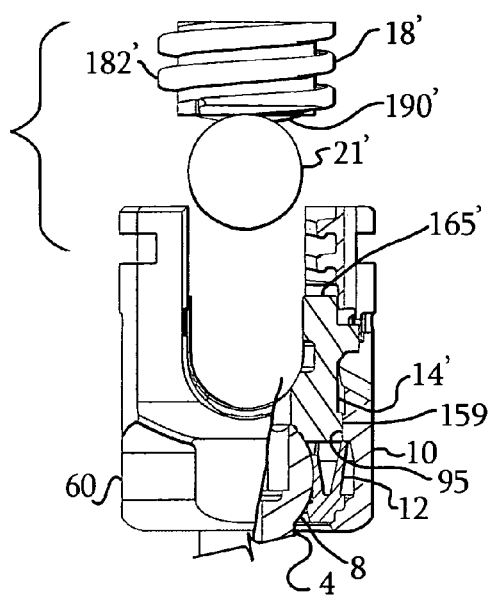
FIG. 38 is a reduced and partial front elevational view with portions broken away, similar to FIG. 37, but with the rod and closure top removed, the locking insert keeping the shank locked in place, the figure further showing an alternative locking insert, a deformable rod and cooperating closure top being installed in the receiver.
Figure 39:
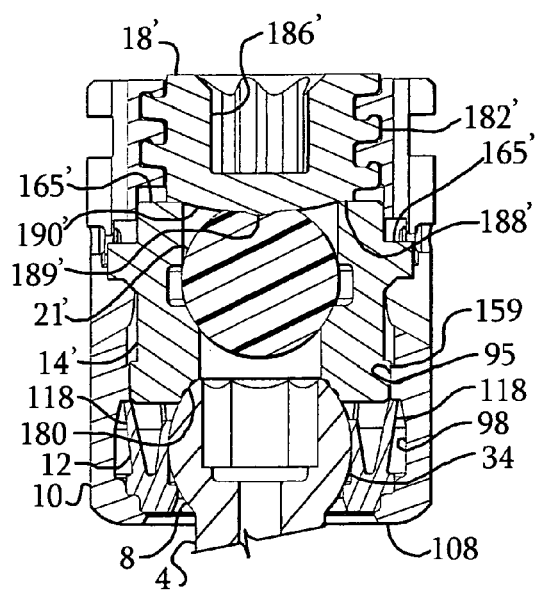
FIG. 39 is an enlarged and partial front elevational view with portions broken away, similar to FIG. 38, showing the alternative rod and closure top fixed to the receiver.

An alternative locking insert 14' shown in FIGS. 38 and 39 includes all the features of the insert 14 with the exception of the grooves 167. Top surfaces 165' of the insert 14' that have more surface area than the surfaces 165 of the insert 14 directly engage the alternative closure top 18' for better locking of the polyaxial mechanism when an alternative deformable rod 21' is being captured between the insert 14' and the closure top 18'.

Returning to the insert 14 shown in FIGS. 17-23, located on the arms 157 and extending outwardly from each surface 160 at a location spaced from the top surfaces 165 are a pair of opposed extensions or wings 168. The wings 168 are partially defined by upper surfaces 169, by outer partially cylindrical surfaces 170 and by lower surfaces 171, the upper surfaces 169 and the lower surfaces 171 being substantially parallel to on another. Opposed side surfaces 172 span between top and bottom surfaces 169 and 171 respectively, of each wing 168, the side surfaces 172 being substantially perpendicular to adjacent top and bottom surfaces 169 and 171. The cylindrical surfaces 170 are sized and shaped for sliding rotation within the receiver arm cylindrical surfaces 92 during assembly of the insert 14 with the receiver 10 as will be described in greater detail below.

Returning to the inner surfaces of the insert 14, a through bore, generally 173, is disposed primarily within and through the body 156 and communicates with a generally U-shaped through channel formed by a saddle surface 174 that is substantially defined by the upstanding arms 157. Near the top surfaces 165, the saddle surface 174 is substantially planar, with the apertures 167 extending thereinto. The saddle 174 has a lower seat 175 sized and shaped to closely, snugly engage the rod 21 or other longitudinal connecting member. It is foreseen that an alternative embodiment may be configured to include planar holding surfaces that closely hold a square or rectangular bar as well as hold a cylindrical rod-shaped, cord, or sleeved tensioned cord longitudinal connecting member. A second set of opposed, inwardly facing apertures 176 are located in the saddle 174 near the lower seat 175 and substantially directly below, but spaced from, the upper grooves or apertures 167. The grooves 176 are sized and shaped to receive tooling for rotation and other manipulation of the insert 14.

The bore, generally 173, is substantially defined at the body 156 by an inner cylindrical surface 177 that communicates with the seat 175 and also communicates with a lower concave, radiused or otherwise curved portion 178 having shank gripping surfaces or ridges 180, the portion 178 generally having a radius for closely mating with the surface 34 of the shank upper portion 8. The portion 178 terminates at the base surface 164. In some embodiments of the invention, the gripping surfaces or ridges 180 are located near the cylindrical surface 177 and a lower part of the portion 178 is a smooth, radiused or spherical surface. In the illustrated embodiment, the gripping ridges or steps 180 are sized and shaped to grip and penetrate into the shank head 8 when the insert 14 is locked against the head surface 34. It is foreseen that there may be more or fewer steps or ridges 180. It is foreseen that the gripping ridges 180 as well as a remainder of the lower shank engaging portion 178 may additionally or alternatively include a roughened or textured surface or surface finish, or may be scored, knurled, or the like, for enhancing frictional engagement with the shank upper portion 8.

The compression insert 14 through bore 173 is sized and shaped to receive a driving tool (not shown) therethrough that engages the shank drive feature 46 when the shank body 6 is driven into bone with the receiver 10 attached. Also, in some locking embodiments of the invention, the bore receives a manipulation tool (not shown) used for releasing the insert from a locked position with the receiver, the tool pressing down on the shank and also gripping the insert at the apertures 176 and/or 167, or with other tool engaging features. Each of the arms 157 and the insert body 156 may include more surface features, such as cut-outs notches, bevels, etc. to provide adequate clearance for inserting the insert 14 into the receiver and cooperating with the retainer 12 during the different assembly steps as will be described in greater detail below.

The insert body 156 cylindrical surface 158 has a diameter slightly smaller than a diameter between crests of the guide and advancement structure 72 of the receiver 10, allowing for top loading of the compression insert 14 into the receiver opening 66, with the arms 157 of the insert 14 being located between the receiver arms 62 during insertion of the insert 14 into the receiver 10. Once the arms 157 of the insert 14 are generally located beneath the guide and advancement structure 72, the insert 14 is rotated into place about the receiver axis B with the wings 168 entering the receiver groove formed by the cylindrical surface 92, the adjacent upper annular surface 91 and the adjacent lower annular surface 93 until the wings are located in the apertures 77 as will be described in greater detail below.

With reference to FIGS. 1 and 35-37, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys, non-metals and deformable and less compressible plastics, including, but not limited to rods made of elastomeric, polyetheretherketone (PEEK) and other types of materials, such as polycarbonate urethanes (PCU) and polyethelenes.

Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 35-37, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes a an outer helically wound guide and advancement structure 182 in the form of a flange that operably joins with the guide and advancement structure 72 disposed on the arms 62 of the receiver 10. The flange form utilized in embodiments according to the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to resist splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the any reduced profile of the receiver 10 that may more advantageously engage longitudinal connecting member components. The illustrated closure structure 18 also includes a top surface 184 with an internal drive 186 in the form of an aperture that is illustrated as a star-shaped internal drive such as that sold under the trademark TORX, or may be, for example, a hex-shaped drive or other internal drives such as slotted, tri-wing, spanner, two or more apertures of various shapes, and the like. A driving tool (not shown) sized and shaped for engagement with the internal drive 186 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 188 of the closure is planar and further includes a rim 190 for engagement and penetration into the surface 22 of the rod 21 in certain embodiments of the invention. It is noted that in some embodiments, the closure top bottom surface 188 may further include a central point for penetration into the rod. It is also noted that other embodiments may or may not include the point and/or the rim. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62.

An alternative closure top, such as the top 18' shown in FIGS. 38 and 39 for use with a deformable rod, such as a PEEK rod 21', for example, includes a bottom surface 188' that has domed portion 190' with a central nub 189' in lieu of the point and rim surface of the closure top 18. Otherwise, the closure top 18' includes a guide and advancement structure 182', a top surface 184' and an internal drive feature 186' the same or substantially similar to the respective guide and advancement structure 182, top surface 184 and internal drive feature 186 of the closure top 18.

The assembly 1 receiver 10, retainer 12 and compression insert 14 are typically assembled at a factory setting that includes tooling for holding and alignment of the component pieces and manipulating the retainer 12 and the insert 14 with respect to the receiver 10. In some circumstances, the shank 4 is also assembled with the receiver 10, the retainer 12 and the compression insert 14 at the factory. In other instances, it is desirable to first implant the shank 4, followed by addition of the pre-assembled receiver, retainer and compression insert at the insertion point. In this way, the surgeon may advantageously and more easily implant and manipulate the shanks 4, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 8 and/or hydroxyapatite on the shank 6), with the receiver, retainer and compression insert. Allowing the surgeon to choose the appropriately sized or treated shank 4 advantageously reduces inventory requirements, thus reducing overall cost and improving logistics and distribution.

Figures 24, 25:
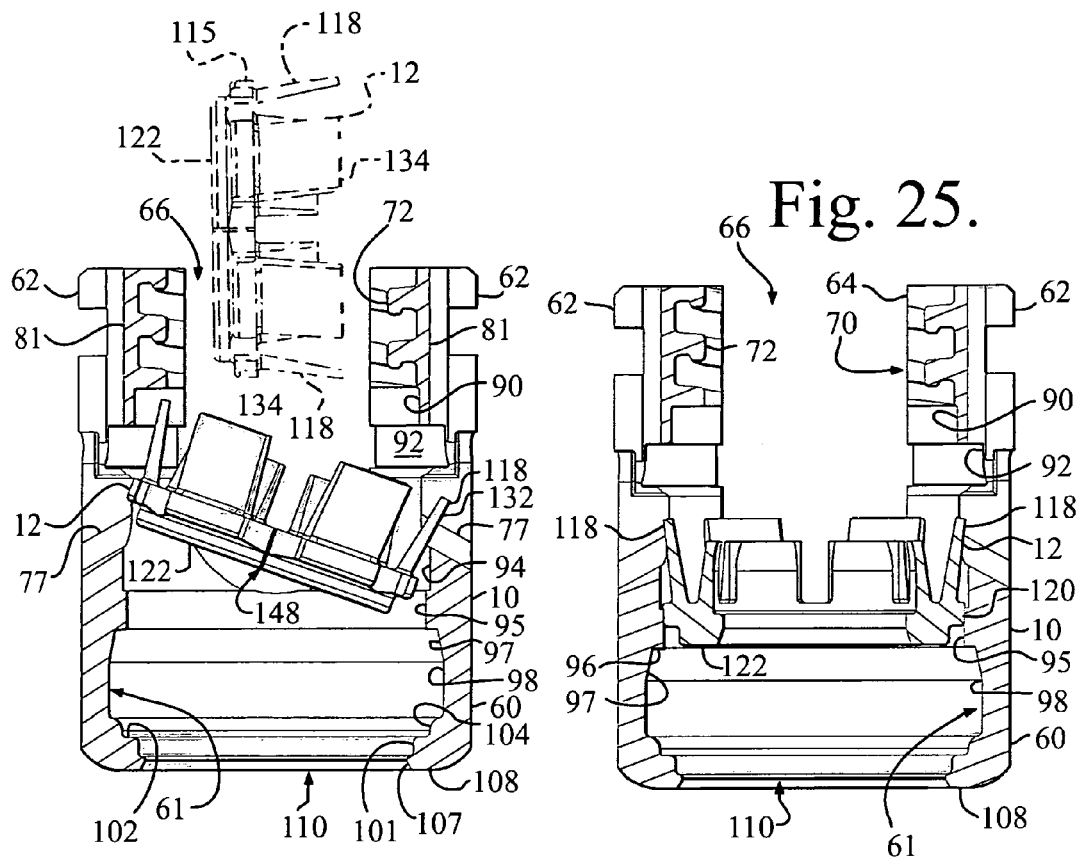
FIG. 24 is an enlarged front elevational view of the retainer and receiver of FIG. 1 with portions of the receiver broken away to show the detail thereof, the retainer being shown downloaded into the receiver (in phantom) to a tipped, partially inserted stage of assembly.
FIG. 25 is a front elevational view of the retainer and receiver with portions broken away, similar to what is shown in FIG. 24, showing the retainer in a subsequent stage of assembly and in a maximum state of compression.
Figure 26:
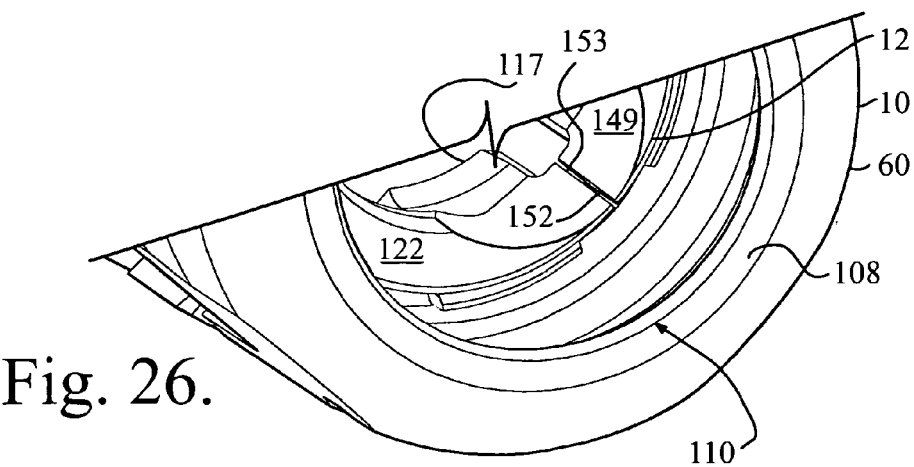
FIG. 26 is an enlarged and partial bottom perspective view of the receiver and retainer of FIG. 25.

Pre-assembly of the receiver 10, retainer 12 and compression insert 14 is shown in FIGS. 24-30. With particular reference to FIG. 24, first the retainer 12 is inserted into the upper receiver opening 66, leading with the outer panels 118 with the panel 118 top surfaces 134 facing one arm 62 and the retainer bottom surface 122 facing the opposing arm 62 (shown in phantom). The retainer 12 is then lowered in such sideways manner into the channel 64 and partially into the receiver cavity 61, followed by tilting the retainer 12 such that at least one outer panel 118 is received into one of the apertures 77 and the opposed panel 118 is located beneath the guide and advancement structure 72. Then, with reference to FIG. 25, the retainer 12 is tilted into a position wherein the central axis of the retainer 12 is generally aligned with the receiver central axis B. As shown in FIG. 25, the retainer outer surfaces 120 engage the receiver inner cylindrical surface 95 and the retainer slit 148 is reduced such that the surfaces 152 and 153 that define the slit 148 are touching or almost touching as shown in FIG. 26 while the surfaces 120 are slid past the receiver surface 95. With reference to FIG. 27, the retainer 12 is pressed downwardly into the receiver to a location wherein the outer tangs 118 resiliently press against the receiver surface 95, holding the retainer within the receiver cavity 61 at a desired temporary position, but not allowing the retainer 12 to drop downwardly onto the receiver seating transition surfaces 104. At this time, the retainer 12 is not yet fully captured within the receiver base cavity 61, but cannot be readily removed unless the panels 118 are squeezed toward one another using a tool or tools.

With further reference to FIG. 27 and with reference to FIGS. 28 and 29, the compression insert 14 is then downloaded into the receiver 10 through the upper opening 66 with the bottom surface 164 facing the receiver arm top surfaces 73 and the insert arm outer surfaces 160 located between the opposed receiver arms 62. The insert 14 is then lowered toward the receiver base 60 until the insert 14 arm upper surfaces 165 are adjacent the run-out area below the guide and advancement structure 72 defined in part by the cylindrical surface 92 and the wings 168 are generally aligned with the receiver groove defined in part by the cylindrical surface 92. Thereafter, the insert 14 is rotated about the receiver axis B until the upper arm surfaces 165 are directly below the guide and advancement structure 72 with the U-shaped channel 173 of the insert 14 aligned with the U-shaped channel 64 of the receiver 10 and the insert wings 168 located at the apertures 77. In some embodiments, the insert arms may need to be compressed slightly during rotation to clear some of the inner surfaces 70 of the receiver arms 62. With particular reference to FIG. 30, at this time, the four crimping wall portions 84 are pressed inwardly towards the insert 14 at either side 172 of each wing 168, the crimping wall material pressing against the insert 14 near the wing sides 172 and thereby prohibiting the insert 14 from rotating with respect to the receiver axis B. At this time, there can be some upward and downward movement of the insert 14, but such movement is limited as the upper wall 82 defining the receiver aperture 77 stops further upward movement of the insert wings 168 and the retainer outer tang top surfaces 134 stop downward movement of the now trapped insert 14. Thus, the frictional engagement between the tangs or panels 118 and the receiver inner surfaces 95 prohibit the retainer 12 and also the insert 14 from dropping further down into the receiver 10 cavity 61. The retainer 12 and the insert 14 are now in a desired position for shipping as an assembly along with the separate shank 4.

Typically, the receiver and retainer combination are shipped or otherwise provided to the end user with the spring-like tangs 118 wedged against the receiver as shown in FIG. 32. The receiver 10, retainer 12 and insert 14 combination is now pre-assembled and ready for assembly with the shank 4 either at the factory, by surgery staff prior to implantation, or directly upon an implanted shank 4 as will be described herein.

As illustrated in FIG. 31, the bone screw shank 4 or an entire assembly 1 made up of the assembled shank 4, receiver 10, retainer 12 and compression insert 14, is screwed into a bone, such as the vertebra 17 (shown in phantom), by rotation of the shank 4 using a suitable driving tool (not shown) that operably drives and rotates the shank body 6 by engagement thereof at the internal drive 46. Specifically, the vertebra 17 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank 4 or the entire assembly 1 is threaded onto the guide wire utilizing the cannulation bore 50 by first threading the wire into the opening at the bottom 28 and then out of the top opening at the drive feature 46. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires and attachable tower tools mating with the receiver. When the shank 4 is driven into the vertebra 17 without the remainder of the assembly 1, the shank 4 may either be driven to a desired final location or may be driven to a location slightly above or proud to provide for ease in assembly with the pre-assembled receiver, compression insert and retainer.

With reference to FIG. 32, the pre-assembled receiver, insert and retainer are placed above the shank upper portion 8 until the shank upper portion is received within the opening 110. With particular reference to FIGS. 32-37, as the shank upper portion 8 is moved into the interior 61 of the receiver base, the shank upper portion 8 presses upwardly against the retainer 12 in the receiver recess partially defined by the cylindrical surface 98, specifically the surface portions 120 press against the surface 98 as the retainer 12 expands about the shank 8. As the shank head 8 continues to move upwardly toward the channel 64, the shank head surface 34 also forces the retainer 12 against the insert 14. However, the insert 14 is prohibited from moving upward by the wing upper surfaces 169 abutting against the surfaces 82 (that is also the ceiling annular surface 91 adjacent the groove 92) defining the apertures 77. Therefore, the upwardly moving shank head 8 forces a widening of the retainer slit 148 and corresponding outward movement of the body 115 of the retainer 12 towards the receiver cylindrical surfaces 98 and stepped or curved surface 104 defining the receiver expansion recess or chamber as best shown in FIG. 33, while the retainer tangs 118 near the top surfaces 134 thereof are generally maintained in a location below the insert 14 bottom surface 164, with the tangs 118 being pressed inwardly toward the axis B at the termination of the receiver wall surface 95. At this time, the spherical surface 34 of the head 8 comes into contact with the retainer inner cylindrical body 145 and the edge 147. With reference to FIG. 34, the retainer 12 begins to return towards a neutral or nominal state as the center of the sphere of the shank head 8 passes beyond the retainer inner edge 147. By the time the hemisphere of the spherical surface 34 extends into a desired captured location within the retainer central bore 141, the shank surface 34 is in contact with the edge 147 as well as with the inner panels 117 at surfaces 129. The combination of the rim or edge 147 surface contact and the panel 117 surfaces 129 contact resiliently pressing against the radiused surface 34, provides a fairly tight friction fit between the head 8 and the retainer 12, the surface 34 being pivotable with respect to the retainer 12 with some force. Thus, a tight, non-floppy ball and socket joint is now created between the retainer 12 and the shank upper portion 8.

With reference to FIG. 35, the receiver is then pulled upwardly or the shank 4 and attached retainer 12 are then moved manually downwardly into a position wherein the retainer tangs 118 are disengaged from the receiver surfaces 95, allowing the tangs 118 to resiliently release and extend outwardly into a neutral or near-neutral position at a location below the receiver annular surface 96 that defines the ceiling of the receiver inner chamber 61. The tangs 118 are now captured within the receiver. Any upward movement of the retainer 12 results in the tang top surfaces 134 abutting against the receiver surfaces 96 and/or 97. However, although fully capture, the retainer 12/shank 4 combination is advantageously only partially restrained with respect to the receiver 10, as a user is able to rotate the retainer 12 about the receiver axis B prior to final locking of the shank head 8 with respect to the receiver 10. At this time also, the retainer surface 121 and bottom surface 122 that forms a lower skirt beneath the retainer body surfaces 120 and 124 are all seated within the stepped surfaces of the receiver. Specifically, the retainer lower surfaces 124 are seated on the receiver annular surface 102 and the bottom surface 122 is seated on the annular surface 103. Downward pressure of the shank head 8 on the retainer edge 147 further expands the retainer body 115 outwardly, with the outer surfaces 120 pressing against the receiver inner cylindrical surface 100 and the lower skirt surface 121 pressing against the receiver inner cylindrical surface 101. The retainer body formed in part by the lower skirt surface 121 advantageously allows for the head 8 to seat lower within the receiver than in other known polyaxial bone anchors. As will be described in greater detail below, the skirt feature that allows for a more stable lower seating surface in combination with the retainer cupped surface 149 that allows for a favored increased or extended angular orientation of the shank with respect to the retainer, and thus with respect to the entire bone screw assembly, allows for such an angular increase without the need to provide a cut-out or cupped surface at and near the receiver bottom 108. Also advantageous is the fact that the partially constrained retainer 12 may be rotated with respect to the receiver 10 about the axis B, allowing for the user to choose the location of the increased angle of orientation between the receiver 10 and the shank 4.

With further reference to FIG. 35, after the retainer 12 is moved downwardly into the receiver 10 and seated on the surfaces 102 and 103, the insert 14 remains located spaced above the shank head 8 as the outer surfaces 159 rest upon the receiver cylindrical surfaces 95, prohibiting downward movement of the insert 14 unless a downward force is applied on the insert either by a tool or the rod 21 and closure top 18, also shown in FIG. 35, for example. It is noted that FIG. 36 simply illustrates the extent of movement of the shank 4 if the shank would be pressed upwardly into the receiver during this stage of assembly. In such case, the retainer 12 would remain in a relatively fixed position due to the outer tangs 118 being blocked from upward movement by the receiver ceiling surface 96. The shank head 8 would abut against the insert 14 at the surface 178 and gripping ridges 180, but the inner tangs 117 would continue to grip the shank spherical surface 34, so a friction fit would still be possible, even if the shank gets moved upwardly. With reference to FIG. 37, downward movement of the closure top 18 presses the rod 21 downwardly that in turn pressed the insert 14 (and possibly the shank 4) downwardly into locking engagement with the retainer 12.

In some embodiments, when the receiver 10 is preassembled with the shank 4, the entire assembly 1 may be implanted by inserting the driving tool (not shown) into the receiver and the shank drive 46 and rotating and driving the shank 4 into a desired location of the vertebra 17. At such time, prior to locking with a closure top, the receiver 10 may be articulated to a desired angular position with respect to the shank 4 (such as the angular orientations shown in FIGS. 40-45, for example), that will be held, but not locked, by the frictional engagement between the retainer 12 inner tangs 117 and the shank upper portion 8. In some cases it may be desirable to lock the insert 14 into the receiver 10 at this time, the insert 14 being pressed downwardly into locking engagement with the shank head 8 by a tool pressing downwardly on the insert, for example, with a tool (not shown) entering through the receiver outer grooves 74 and pressing downwardly on the insert wings 168. Such a tool may also include (or alternatively be) a structure for gripping the receiver, for example, a pronged tool or tool portion with some of the tool extending into the receiver channel 64. Or, as explained above, the insert 14 may remain spaced above the shank head 8 until locked into place by the rod 21 and the closure top 18 pressing down upon the insert 14.

As explained above and as best shown in FIGS. 35 and 37, the diameter of the insert outer surface or band 159 is sized large enough to require that the surface 159 must be forced into the cylindrical surface 95 of the receiver by a tool or tools or by the closure top 18 forcing the rod 21 downwardly against the insert 14 with sufficient force to interferingly frictionally lock or wedge the insert 14 into the receiver 10 at the surface 159. This independent lock-and-release feature gives the surgeon flexibility to loosen the closure top and even remove the closure top and rod without affecting the locking of the polyaxial mechanism of the assembly 1, the anchor assembly functioning like a fixed monoaxial screw with the shank 4 in fixed relation with the receiver 10, but with the shank remaining in a desired angle with respect to the receiver. Thus, once a locking insert is in an interference fit locking engagement with the receiver as shown in FIG. 37, if a rod and closure top have been assembled with the receiver 10, the closure top 18 may be loosened or removed and/or the rod 21 may be adjusted and/or removed and the frictional engagement between the insert 14 and the receiver 10 at the receiver surface 95 will remain locked in place, advantageously maintaining a locked angular position of the shank 4 with respect to the receiver 10. At such time, another rod, such as a deformable rod 21' and cooperating alternative closure top 18' may be loaded onto the already locked-up assembly to result in an alternative assembly.

With reference to FIGS. 38 and 39, there is illustrated an alternative insert 14' that is identical to the insert 14 with the exception that an upper surface 165' is sized and shaped for direct engagement with the alternative closure top 18'. The illustrated rod 21' has the same or similar dimensions as the rod 21, with a cylindrical surface 22', but is made from a material, such as PEEK, that deforms in response to pressure from the closure top, thus making the closure top 18' having the domed surface 190' and central nub 189' a more desirable locking mechanism for keeping the deformable rod 18' in place within the receiver 10. Because the locking of the polyaxial mechanism of the assembly is not dependent on the force of the rod 21' and closure top 18' on the insert 14, any further deformation or eventual loosening of the rod with respect to the closure top 18' or the insert 14' does not affect the secure locking between the insert 14 and the receiver 10 and thus the shank 4 stays frictionally locked against both the insert 14 and the retainer 12, locking the shank 4 in a desired angular position with respect to the receiver 10.

If unlocking of the insert 14 or 14' with respect to the receiver 10 is desired, a tool (not shown) may be inserted into the through apertures 77 below the insert wings 168 and the insert 14 or 14' may be pulled away from the receiver 10. Such a tool may include a piston-like portion for pushing directly on the shank while the insert 14 is pulled away from the receiver. At such time, the shank 4 may be articulated with respect to the receiver 10, and the desired friction fit returns between the retainer 12 and the shank surface 34, so that an adjustable, but non-floppy relationship still exists between the shank 4 and the receiver 10. If further disassembly if the assembly is desired, such is accomplished in reverse order to the procedure described previously herein for the assembly 1.

Returning to FIGS. 35 and 36, the rod 21 is positioned in an open or percutaneous manner in cooperation with the at least two bone screw assemblies 1. The closure structure 18 is then advanced between the arms 62 of each of the receivers 10. The closure structure 18 is rotated, using a tool engaged with the inner drive 186 until a selected pressure is reached at which point the rod 21 engages the U-shaped saddle 173 of the compression insert 14, further pressing the insert spherical surface 178 and stepped shank gripping surfaces 180 against the shank spherical surface 34, the edges 180 penetrating into the spherical surface 34, pressing the shank upper portion 8 into locked frictional engagement with the retainer 12. Specifically, as the closure structure 18 rotates and moves downwardly into the respective receiver 10, the rim 190 engage and penetrate the rod surface 22, the closure structure 18 pressing downwardly against and biasing the rod 21 into compressive engagement with the insert 14 that urges the shank upper portion 8 toward the retainer 12 and into locking engagement therewith at the retainer edge surface 147, the retainer 12 frictionally abutting the receiver surfaces 102 and 103 and pressing outwardly against the receiver cylindrical surfaces 100 and 101. For example, about 80 to about 120 inch pounds of torque on the closure top may be applied for fixing the bone screw shank 6 with respect to the receiver 10. At this time, the retainer inner edge 147 engages and digs into the shank head 8. At this time, the inner tangs 117 may be slightly spaced from the shank head 8 or may be still touching the shank spherical surface 34, but are no longer in tight or close frictional engagement with the surface 34 and thus are not participating in the final locking engagement between the shank 4 and the retainer 12. As best shown in FIG. 37, due to the position and geometry of the lower skirt surfaces 121 and 122 with respect to the receiver 10 and also due to the location of the inner edge 147, the shank head 8 sits low in the receiver cavity 61, allowing for desirable increased articulation of the shank 4 with respect to the retainer 12 and thus with respect to the receiver 10 as compared to a retainer that does not include such a lower skirt, for example. If disassembly if the assembly 1 is desired, such is accomplished in reverse order to the procedure described previously herein for assembly.

Figure 40:
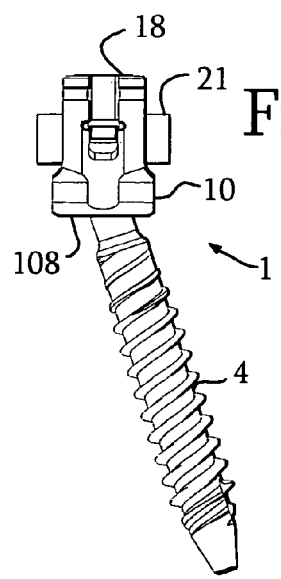
FIG. 40 is a reduced side elevational view of the assembly of FIG. 1, shown fully assembled with the shank disposed at an eighteen degree (cephalad) angle with respect to the receiver.
Figure 41:
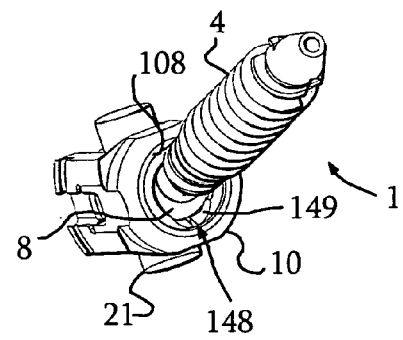
FIG. 41 is an enlarged perspective view of the assembly of FIG. 40.
Figure 42:
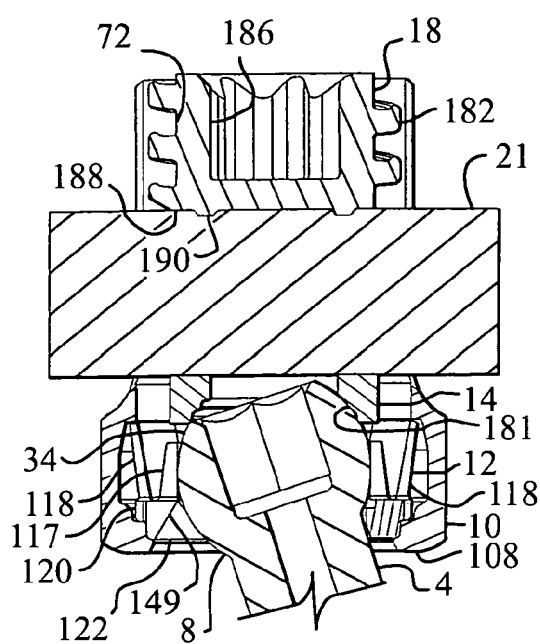
FIG. 42 is an enlarged and partial side elevational view of the assembly of FIG. 40 with portions broken away to show the detail thereof.
Figure 43:
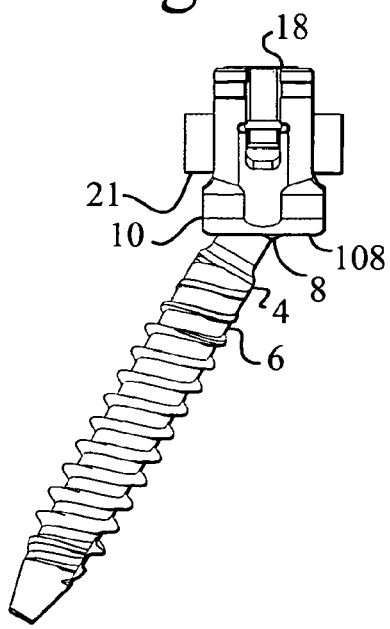
FIG. 43 is a reduced side elevational view of the assembly of FIG. 1, shown fully assembled with the shank disposed at a thirty degree (caudad) angle with respect to the receiver.
Figure 44:
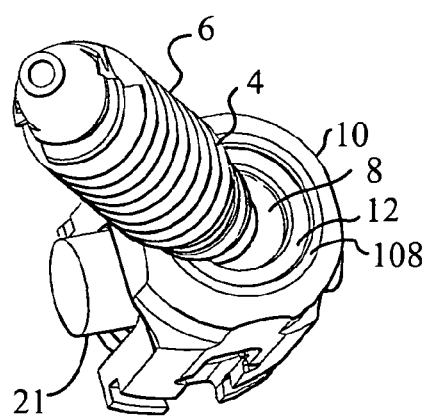
FIG. 44 is an enlarged perspective view of the assembly of FIG. 43.
Figure 45:
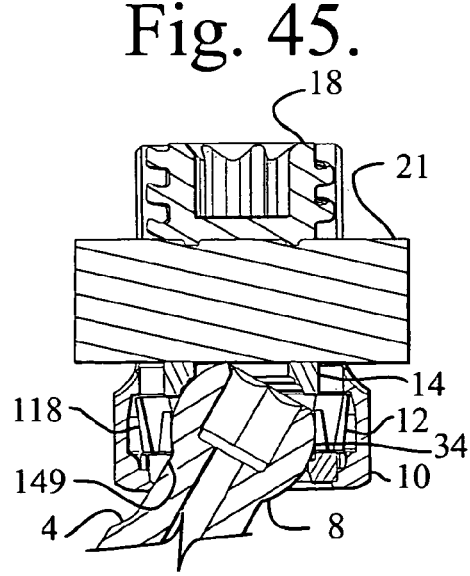
FIG. 45 is an enlarged and partial side elevational view of the assembly of FIG. 43 with portions broken away to show the detail thereof.
Figure 46:
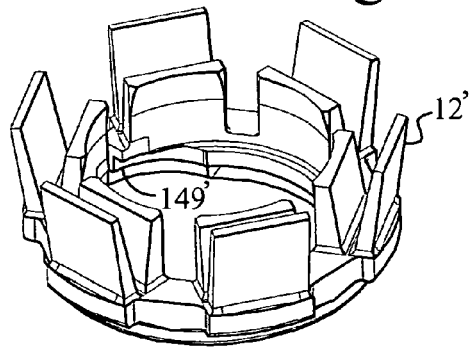
FIG. 46 is an enlarged perspective view of an alternative retainer for use in lieu of the retainer in the assembly of FIG. 1.
Figure 47:
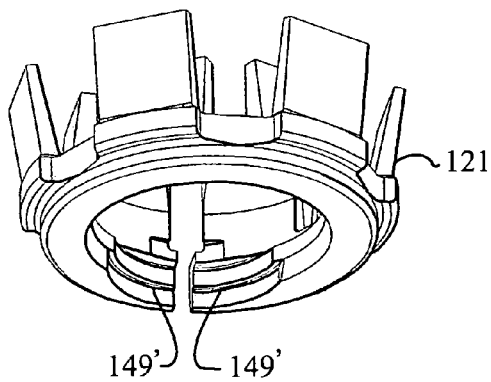
FIG. 47 is another perspective view of the retainer of FIG. 46.
Figure 48:
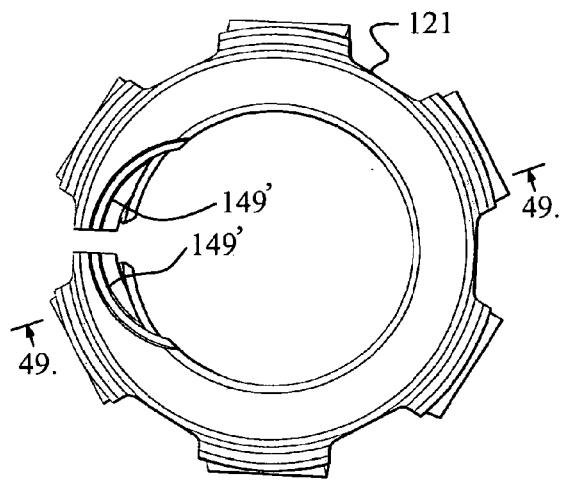
FIG. 48 is en enlarged bottom plan view of the retainer of FIG. 46.
Figure 49:
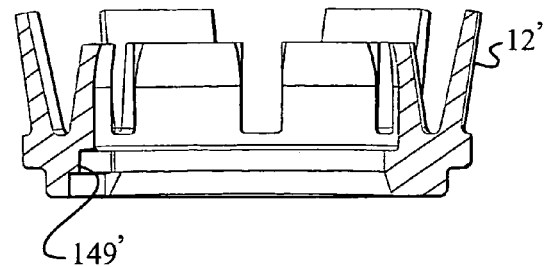
FIG. 49 is a cross-sectional view taken along the line 49-49 of FIG. 48.

With reference to FIGS. 40-45, different angular or articulated positions of the shank 4 with respect to the receiver 10 are shown, some making full use of the slit 148 and adjacent cut-out or cupped surfaces 149 of the retainer 12. For example, compare FIGS. 43-45 wherein the shank 8 is pivoted toward and into engagement with the cupped surfaces 149 as compared to the arrangement shown in FIGS. 40-42, wherein the shank 4 is pivoted in a direction opposite to the retainer slit 148. In FIGS. 40-42 wherein the shank is pivoted in a direction away from the slit 148 and cupped surfaces 149, a resulting shank to receiver articulation is about eighteen degrees (cephalad, for example), which is a desirable degree of articulation in some instances. FIGS. 43-45 show a thirty degree (caudad) or slightly further articulation, possible when the shank head 8 abuts against both surfaces 149 as well as moving slightly into the gap formed by the slit 148.

Figure 50:
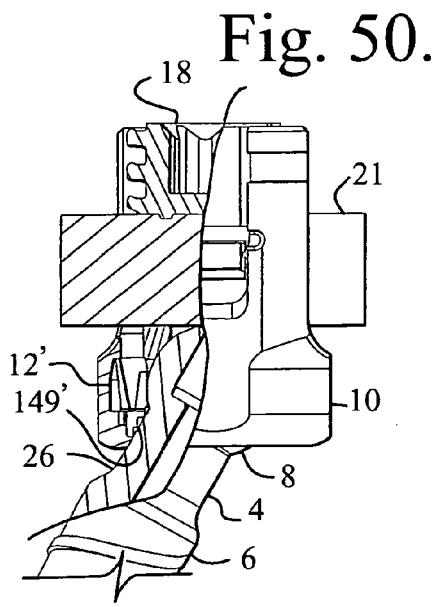
FIG. 50 is an enlarged and partial side elevational view of the assembly of FIG. 1 modified to include the retainer of FIG. 46 in lieu of the retainer shown in FIG. 1, and shown with portions broken away to show the detail thereof.
Figure 51:
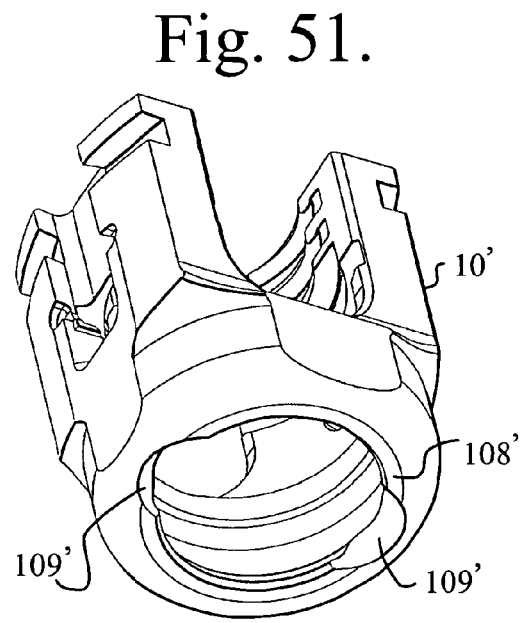
FIG. 51 is an enlarged perspective view of an alternative extended or favored angle receiver of an embodiment according to the invention having opposed lower concave surfaces for cooperating with the retainer of FIG. 1 to allow for up to a forty degree angle of the shank of FIG. 1 with respect to the alternative receiver.
Figure 52:
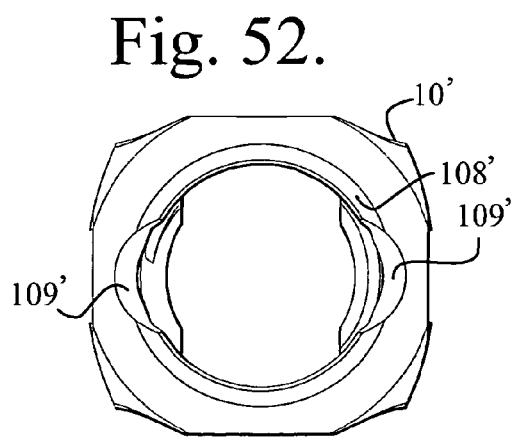
FIG. 52 is an enlarged bottom plan view of the alternative receiver of FIG. 51.
Figure 53:
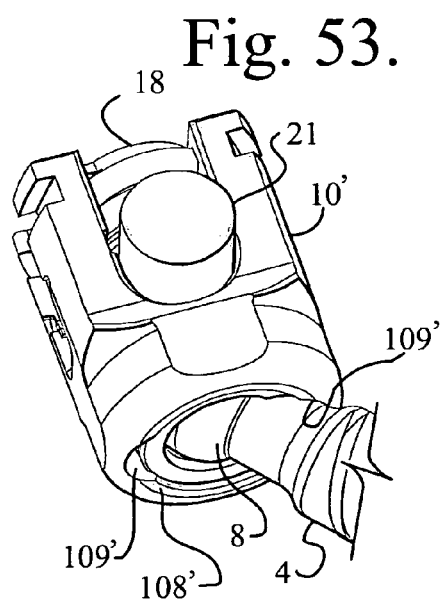
FIG. 53 is an enlarged perspective view of the assembly of FIG. 1 modified to include the alternative receiver of FIG. 51 in lieu of the receiver shown in FIG. 1.
Figure 54:
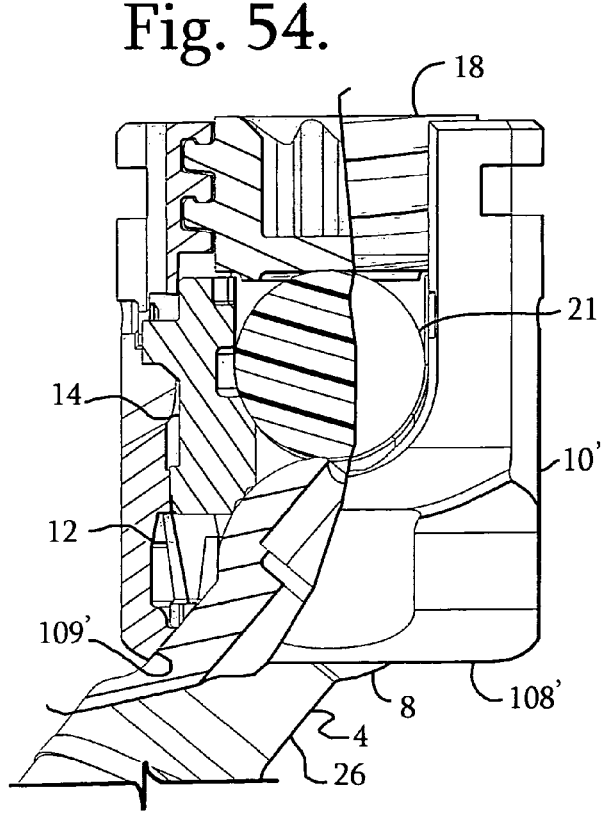
FIG. 54 is an enlarged and partial front elevational view of the assembly of FIG. 53 with portions broken away to show the detail thereof.

FIGS. 46-50 illustrate an alternative retainer 12' that includes cupped or cut-out surfaces 149' that are graduated or stepped as compared to the smooth surfaces 149 of the retainer 12. Otherwise, the retainer 12' is identical or substantially similar in form and function to the retainer 12 previously discussed herein. Thus, the retainer 12' fully cooperates with the receiver 10, insert 14, shank 4, rod 21 and closure top 18 in a manner substantially identical to what has been described above with respect to the assembly 1, with the exception that the stepped surfaces 149' grip or dig into the shank 4 at the neck 26 when the shank is pivoted to an about thirty degree articulation with respect to the receiver as shown in FIG. 50. It is foreseen that greater or fewer stepped surfaces may be included along the cupped surface portion 149'.

Figure 55:
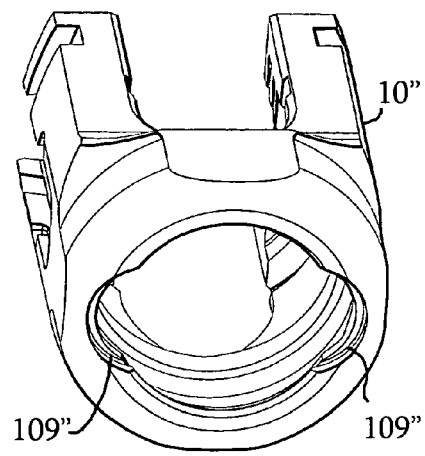
FIG. 55 is a perspective view of another alternative extended or favored angle embodiment of a receiver according to the invention, similar to the receiver of FIG. 51, but having lower concave stepped surfaces.
Figure 56:
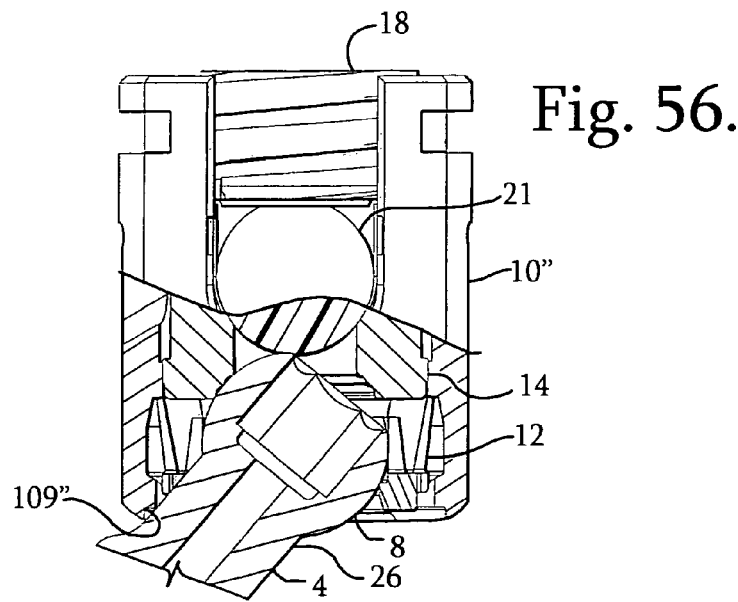
FIG. 56 is an enlarged and partial front elevational view of the assembly of FIG. 1 modified to include the alternative receiver of FIG. 55 in lieu of the receiver shown in FIG. 1.

FIGS. 51-54 illustrate an alternative receiver 10' that includes a bottom surface 108' further defined by a pair of opposed, concave curved bottom surfaces 109'. Otherwise, the receiver 10' is identical to the receiver 10 described above and thus fully cooperates with the retainer 12, insert 14, shank 4, rod 21 and closure top 18 in a manner substantially identical to what has been described above with respect to the assembly 1. FIGS. 55-56 illustrate another alternative receiver 10" that is substantially similar to the receiver 10', also having opposed, concave curved bottom surfaces 109". The receiver 10" differs from the receiver 10' only in that the surfaces 109" are graduated or stepped. Just like the receiver 10, when the retainer 12 is fully assembled with the receiver 10' or the receiver 10", the retainer 12 is captured within the receiver inner cavity, but is only partially constrained therein, the retainer being rotatable about the central axis of the receiver 10' or 10". Thus, the retainer 12 slit 148 and surfaces 149 can be aligned with either of the receiver concave surfaces 109' or 109". When the retainer surfaces 149 are aligned with one of the surfaces 109' or 109", at least a forty degree angle of articulation between the shank 4 and the receiver 10' or 10" is possible.

Figure 57:
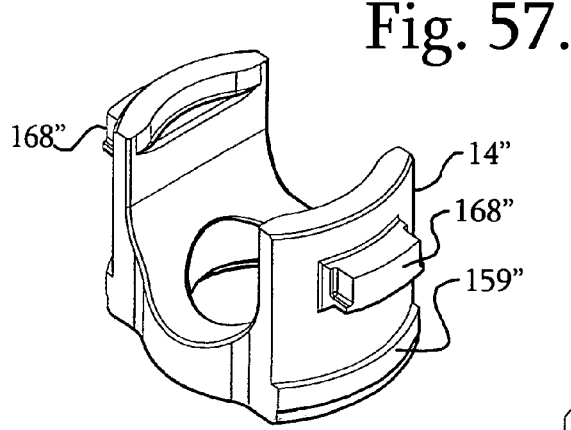
FIG. 57 is an enlarged perspective view of an alternative non-locking embodiment of an insert according to the invention for use in lieu of the locking insert shown in FIG. 1.
Figure 58:
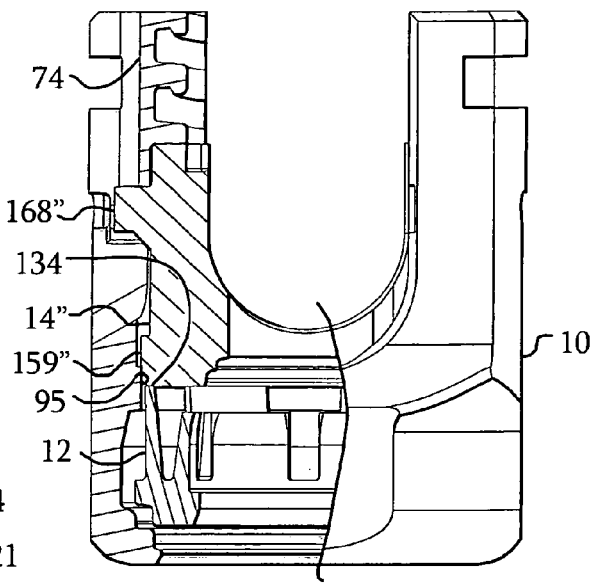
FIG. 58 is an enlarged front elevational view of the receiver and retainer of FIG. 1 shown in a stage of assembly with the alternative insert of FIG. 57, also in front elevation, with portions broken away to show the detail thereof.
Figure 59:
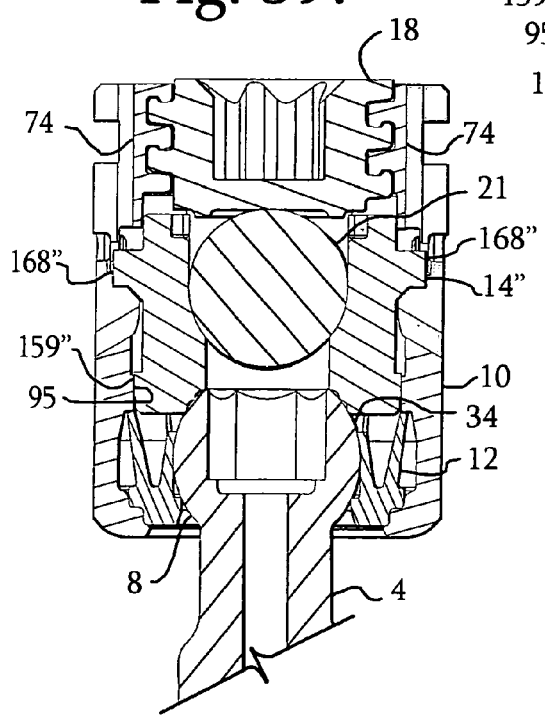
FIG. 59 is an enlarged and partial front elevational view of the receiver, retainer, rod and closure top of FIG. 1 shown fully assembled with the alternative insert of FIG. 57, also in front elevation, with portions broken away to show the detail thereof.

With reference to FIGS. 57-59, an alternative non locking compression insert 14' is illustrated for use with the shank 4, receiver 10, retainer 12, closure top 18 and rod 21 previously described herein. The insert 214 is substantially similar to the insert 14 previously described herein, having all the features of the insert 14 with the exception of the through apertures 167 and the enlarged interference fit surface 159. Instead, the insert includes an other lower surface or band 159" having a diameter sized to easily slidingly fit within the receiver surface 95 rather than interferingly fit with such surface. The insert 14" is assembled with the receiver 10, retainer 12, shank 4, rod 21 and closure top 18 in a manner the same as previously described above with respect to the assembly 1, with the exception that the insert 14" need not be forced downwardly into a locking interference fit with the receiver 10 when the shank 4 is locked in place. If the closure top 18 is loosened or if the closure top 18 and the rod 21 are removed from the assembly 1, the insert 14" will also shift upwardly in the receiver 10 and the shank 4 will not remain locked with respect to the retainer 12 and the receiver 10. Tooling (not shown) cooperating with the receiver grooves 74 to press downwardly on wings 168" of the insert 14" advantageously provides for a temporary locking of the polyaxial mechanism during surgery, if desired by the surgeon.

It is to be understood that while certain forms of the present invention have been illustrated and described herein, it is not to be limited to the specific forms or arrangement of parts described and shown.

What is claimed and desired to be secured by Letters Patent is as follows:

1. A pivotal bone anchor assembly for securing an elongate rod to a bone, the bone anchor assembly comprising:
   a bone anchor having a proximal portion with an at least partially spherical outer surface and an anchor portion extending distally from the proximal portion for attachment to the bone;
   a receiver comprising a base defining an internal cavity having a bottom opening in communication with a bottom surface of the base, and a pair of integral arms extending upwardly from the base to define a U-shaped upper channel having inner sidewall surfaces configured to receive the elongate rod, the upper channel communicating with the internal cavity to define a central bore, the internal cavity having a wider upper portion and a lower locking portion below the wider upper portion defined by a narrower width of the internal cavity adjacent the bottom opening, the central bore including an inwardly-facing interference wedging surface;
   a retainer disposed within the wider upper portion of the internal cavity, the retainer having an interior surface operable to grip the at least partially spherical outer surface of the bone anchor proximal portion, the retainer allowing the bone anchor proximal portion to be received therein as it is uploaded through the bottom opening and then close around and capture the bone anchor proximal portion within the internal cavity while allowing for pivotal motion of the bone anchor relative to the receiver; and
   a pressure insert positioned within the upper channel above the retainer and having an upper curved saddle seating surface aligned with the upper channel, the curved saddle seating surface being sized and shaped for engaging the elongate rod, the insert including an inward facing groove formed therein for receiving tooling,
   wherein after the bone anchor proximal portion is captured, the pressure insert is downwardly deployable with a first tool within the receiver until an outer surface of the pressure insert comes into a forced interference wedging contact with the receiver interference wedging surface, and
   wherein the forced interference wedging contact between these surfaces inhibits the pressure insert from moving back up within the receiver cavity until released and moved back up by a second tool.

2. The bone anchor assembly of claim 1, wherein the pressure insert is upwardly retrievable from the forced interference wedging contact using the second tool to release the bone anchor from a fixed angular position relative to the receiver.

3. The bone anchor assembly of claim 1, wherein the second tool is configured to grip the pressure insert at the inward facing groove.

4. The bone anchor assembly of claim 1, wherein the pressure insert has a generally elongate shape with rounded ends, as viewed from above, with a long axis extending perpendicular to an axis of the curved saddle seating surface.

5. The bone anchor assembly of claim 1, wherein the retainer is non-pivoting with respect to the receiver after the bone anchor proximal portion is secured therein.

6. The bone anchor assembly of claim 1, wherein the retainer frictionally engages the bone anchor proximal portion upon capture within the internal cavity to allow for an unlocked but non-floppy positioning of the bone anchor relative to the receiver prior to a final locking of the pivotal bone anchor assembly.

7. The bone anchor assembly of claim 1, wherein the retainer includes at least one slot extending from a top to a bottom surface thereof.

8. The bone anchor assembly of claim 7, wherein the retainer is an open resilient ring.

9. The bone anchor assembly of claim 1, further comprising a closure having a receiver-mating structure formed into an outer sidewall surface thereof engageable with a complimentary closure-mating structure formed into the inner sidewall surfaces of the upwardly-extending arms to capture the elongate rod within the U-shaped upper channel.

10. The bone anchor assembly of claim 9, wherein the closure receiver-mating structure and the receiver closure-mating structure each comprise complimentary helical threads formed on the outer sidewall surface of the closure and the inner sidewall surface of the receiver, respectively.

11. The bone anchor assembly of claim 10, wherein the pressure insert is downwardly deployable within the receiver into the forced interference wedging contact with the receiver interference wedging surface upon engagement of the closure within the receiver upwardly-extending arms to secure the elongate rod within the U-shaped upper channel.

12. The bone anchor assembly of claim 1, wherein the receiver is attachable to the bone anchor proximal portion after the anchor portion is fixed to the bone.

13. The bone anchor assembly of claim 1, wherein the pressure insert is positioned within the receiver before the bone anchor proximal portion is uploaded through the bottom opening of the receiver cavity.

14. A pivotal bone anchor assembly for securing an elongate rod to a bone, the bone anchor assembly comprising:
   a bone anchor having an upper portion with an at least partially spherical outer surface and an integral anchor portion extending distally from the upper portion for fixation to the bone; and
   a receiver assembly in a pre-assembled configuration for receiving the upper portion of the bone anchor, the receiver assembly including:
      a receiver comprising a base defining an internal cavity having a bottom opening in communication with a bottom surface of the base, and a pair of integral arms extending upwardly from the base to define a U-shaped channel having inner sidewall surfaces configured to receive the elongate rod, the U-shaped channel communicating with the internal cavity to define a central bore, the internal cavity having a wider upper portion and a narrower lower locking portion below the wider upper portion defined by a narrowing restriction in a width of the internal cavity adjacent the bottom opening, the central bore including an inwardly-facing interference wedging surface;
      a retainer having a concave interior surface operable to grip the at least partially spherical outer surface of the bone anchor upper portion, the retainer being initially disposed within the wider upper portion of the internal cavity and being able to separate to receive the bone anchor upper portion therein as it is uploaded through the bottom opening and then close around and capture the bone anchor upper portion within the internal cavity while allowing for pivotal motion of the bone anchor relative to the receiver; and a pressure insert positioned within the U-shaped channel above the retainer and having an upper curved saddle seating surface aligned with the U-shaped channel, the curved saddle seating surface being sized and shaped for engaging the elongate rod, the insert further including an inward facing groove formed therein for receiving tooling, wherein after the bone anchor upper portion is captured, the pressure insert is downwardly deployable with a first tool within the receiver until an outer surface of the pressure insert comes into a forced interference wedging contact with the receiver interference wedging surface, and wherein the forced interference wedging contact between these surfaces inhibits the pressure insert from moving back up within the receiver cavity until released and moved back up by a second tool.

15. The bone anchor assembly of claim 14, wherein the pressure insert is upwardly retrievable from the forced interference wedging contact using the second tool to release the bone anchor from a fixed angular position relative to the receiver.

16. The bone anchor assembly of claim 14, wherein the second tool is configured to engage the pressure insert at the inward facing groove.

17. The bone anchor assembly of claim 14, wherein the pressure insert has a generally elongate shape with rounded ends, as viewed from above, with a long axis extending perpendicular to an axis of the curved saddle seating surface.

18. The bone anchor assembly of claim 14, wherein the retainer is non-pivoting with respect to the receiver after the bone anchor upper portion is secured therein.

19. The bone anchor assembly of claim 14, wherein the retainer frictionally engages the bone anchor upper portion upon capture within the internal cavity to allow for an unlocked but non-floppy positioning of the bone anchor relative to the receiver prior to a final locking of the pivotal bone anchor assembly.

20. A pivotal bone anchor assembly for securing an elongate rod to a bone, the bone anchor assembly comprising:
   a bone anchor having an upper portion with an at least partially spherical outer surface and an integral anchor portion extending distally from the upper portion for fixation to the bone; and
   a receiver assembly in a pre-assembled configuration for receiving the upper portion of the bone anchor, the pre-assembled configuration for the receiver assembly including:
      a receiver comprising a base defining an internal cavity having a bottom opening in communication with a bottom surface of the base, and a pair of integral arms extending upwardly from the base to define a U-shaped channel having inner sidewall surfaces configured to receive the elongate rod, the U-shaped channel communicating with the internal cavity to define a central bore, the internal cavity having an expansion portion and a locking portion below the expansion portion defined by a restriction in the diameter of the internal cavity adjacent the bottom opening, the central bore including an inwardly-projecting wedging surface;
      a retainer having a plurality of clamping portions with interior surfaces operable to grip the at least partially spherical outer surface of the bone anchor upper portion, the retainer being disposed within the expansion portion of the internal cavity and being expandable to receive and snap around the bone anchor upper portion as it is uploaded through the bottom opening to capture the bone anchor upper portion within the internal cavity while allowing for pivotal motion of the bone anchor relative to the receiver; and
      a pressure insert positioned within the U-shaped channel above the retainer and having an upper curved saddle aligned with the U-shaped channel, the curved saddle being sized and shaped for engaging the elongate rod and including a pair of opposed, inward facing grooves formed therein for receiving tooling,
   wherein the retainer and pressure insert are downwardly deployable within the receiver until an outer surface of the retainer engages the restriction in the receiver locking portion and an outer surface of the pressure insert becomes wedged against the receiver wedging surface, so as to lock the bone anchor into a fixed angular position relative the receiver body and to prevent the pressure insert and the retainer from moving back up within the internal cavity.

21. The bone anchor assembly of claim 20, wherein the pressure insert is downwardly deployable within the receiver to the wedged locking position using a first tool.

22. The bone anchor assembly of claim 20, wherein the pressure insert is upwardly retrievable from the wedged locking position using a second tool to release the bone anchor from a fixed angular position relative to the receiver.

23. The bone anchor assembly of claim 22, wherein the second tool is configured to grip the pressure insert by the opposed, inward facing grooves formed into the upper curved saddle.

* * * * *